United States Patent
Quinn

(10) Patent No.: US 6,420,155 B1
(45) Date of Patent: Jul. 16, 2002

(54) AORTIC CARBOXYPEPTIDASE-LIKE PROTEIN AND NUCLEIC ACIDS ENCODING SAME

(75) Inventor: Kerry E. Quinn, Hamden, CT (US)

(73) Assignee: Curagen Corporation, New Haven, CT (US)

( * ) Notice: Subject to any disclaimer, the term of this patent is extended or adjusted under 35 U.S.C. 154(b) by 0 days.

(21) Appl. No.: 09/641,741

(22) Filed: Aug. 18, 2000

Related U.S. Application Data

(60) Provisional application No. 60/159,613, filed on Oct. 14, 1999, provisional application No. 60/175,534, filed on Jan. 11, 2000, and provisional application No. 60/224,086, filed on Aug. 9, 2000.

(51) Int. Cl.$^7$ .............................. C12N 9/48; C12N 1/20; C12Q 1/00; A61K 38/46; C07H 21/04
(52) U.S. Cl. ........................ 435/212; 435/6; 435/252.3; 435/320.1; 435/536; 435/23.2; 435/424; 435/94.6
(58) Field of Search ........................ 424/94.6; 435/212, 435/252.3, 320.1, 6; 536/23.2

(56) References Cited

U.S. PATENT DOCUMENTS 5,460,951 A * 10/1995 Kawai et al. ............... 435/69.1
6,140,098 A * 10/2000 Balasubramanian ........ 435/219

OTHER PUBLICATIONS

Brownstein, M. J., J. T. Russell, et al. (1980). "Synthesis, transport, and release of posterior pituitary hormones." *Science* 207(4429): 373–8.

DeCruz, E. E., T. L. Walker, et al. (1996). "The basis for somatic gene therapy of cancer." *J Exp Ther Oncol* 1(2): 73–83. Abstract Only.

Fricker, L. D. and E. H. Leiter (1999). "Peptides, enzymes and obesity: new insights from a 'dead' enzyme." *Trends Biochem Sci* 24(10): 390–3.

He, et al., 1995 "A eukaryotic transcriptional repressor with carboxypeptidase activity." *Nature* 378: 92–96. GenBank Accession No. Q61281.

Layne, et al., 1998 "Aortic carboxypeptidase–like protein, a novel protein with discoidin and carboxypeptidase–like domains, is up–regulated during vascular smooth muscle cell differentiation." *J. Biol. Chem.* 273: 15654–45660. GenBank Accession No. O14113.

Layne, et al., 1998 "Aortic carboxypeptidase–like protein, a novel protein with discoidin and carboxypeptidase–like domains, is up–regulated during vascular smooth muscle cell differentiation." *J. Biol. Chem.* 273: 15654–45660. GenBank Accession No. Q88442.

Layne, M. D., W. O. Endege, et al. (1998). "Aortic carboxypeptidase–like protein, a novel protein with discoidin and carboxypeptidase–like domains, is up–regulated during vascular smooth muscle cell differentiation." *J Biol Chem* 273(25): 15654–60.

Lei, et al., 1999 "Identification of mouse CPX–1, a novel member of the metallocarboxypeptidase gene family with highest similarity to CPX–2." *DNA Cell* Biol 18 (2): 175–185. GenBank Accession No. AF077738.

Lei, et al., 1999 "Identification of mouse CPX–1, a novel member of the metallocarboxypeptidase gene family with highest similarity to CPX–2." *DNA Cell* Biol 18 (2): 175–185. GenBank Accession No. Q9Z100.

Lei, Y., X. Xin, et al. (1999). "Identification of mouse CPX–1, a novel member of the metallocarboxypeptidase gene family with highest similarity to CPX–2." *DNA Cell Biol* 18(2): 175–85.

Mandriota, et al., 1998 "Regulation of angiopoietin–2 mRNA levels in bovine microvascular endothelial cells by cytokines and hypoxia." *Circ Res.* 83: 852–859. GenBank Accession No. ALO35460.

McGwire, G. B., F. Tan, et al. (1997). "Identification of a membrane–bound carboxypeptidase as the mammalian homolog of duck gp 180, a hepatitis B virus–binding protein." *Life Sci* 60(10): 715–24.

Muise, A. M. and H. S. Ro (1999). "Enzymic characterization of a novel member of the regulatory B–like carboxypeptidase with transcriptional repression function: stimulation of enzymic activity by its target DNA." *Biochem J* 343 Pt 2: 341–5.

Naggert, J. K., L. D. Fricker, et al. (1995). "Hyperproinsulinaemia in obese fat/fat mice associated with a carboxypeptidase E mutation which reduces enzyme activity." *Nat Genet* 10(2): 135–42. Abstract Only.

Ohno, I., J. Hashimoto, et al. (1996). "A cDNA cloning of human AEBPI from primary cultured osteoblasts and its expression in a differentiating osteoblastic cell line." *Biochem Biophys Res Commun* 228(2): 411–4.

Olias, G., D. Richter, et al. (1996). "Heterologous expression of human vasopressin–neurophysin precursors in a pituitary cell line: defective transport of a mutant protein from patients with familial diabetes insipidus." *DNA Cell Biol* 15(11): 929–35.

Rehli, M., S. W. Krause, et al. (1995). "Carboxypeptidase M is identical to the Max.1 antigen and its expression is associated with monocyte to macrophage differentiation." *J Biol Chem* 270(26): 15644–9.

Repaske, D. R. and J. E Browning (1994). "A de novo mutation in the coding sequence for neurophysin–II (Pro24—>Leu) is associated with onset and transmission of autosomal dominant neurohypophyseal diabetes insipidus." *J Clin Endocrinol Metab* 79(2): 421–7.

(List continued on next page.)

Primary Examiner—Elizabeth Slobodyansky
Assistant Examiner—Yong Pak
(74) Attorney, Agent, or Firm—Mintz, Levin, Cohn, Ferris, Glovsky and Popeo; Ivor R. Elrifi; Cynthia A. Kozakiewicz

(57) ABSTRACT

Disclosed are nucleic acids encoding aortic carboxypeptidase-related polypeptides, polypeptides encoded by these nucleic acids, and methods of using these nucleic acids and polypeptides.

2 Claims, 12 Drawing Sheets

OTHER PUBLICATIONS

Sachs, H., P. Fawcett, et al. (1969). "Biosynthesis and release of vasopressin and neurophysin." *Recent Prog Horm Res* 25: 447–91.

Saez, E., D. No, et al. (1997). "Inducible gene expression in mammalian cells and transgenic mice." *Curr Opin Biotechnol* 8(5): 608–16.

Sawada, M. and T. Kamataki (1998). "Genetically engineered cells stably expressing cytochrome P450 and their application to mutagen assays." *Mutat Res* 411(1): 19–43.

Schmale, H., R. Ivell, et al. (1984). "The mutant vasopressin gene from diabetes insipidus (Brattleboro) rats is transcribed but the message is not efficiently translated." *Embo J* 3(13): 3289–93.

Seed, B. (1987). "An LFA–3 cDNA encodes a phosholipid–linked membrane protein homologous to its receptor CD2." *Nature* 329(6142): 840–2. Abstract Only.

Song, L. and L. D. Fricker (1997). "Cloning and expression of human carboxypeptidase Z, a novel metallocarboxypeptidase." *J Biol Chem* 272(16): 10543–50.

Tan, F., H. Jackman, et al. (1989). "Protamine inhibits plasma carboxypeptidase N, the inactivator of anaphylatoxins and kinins." *Anesthesiology* 70(2): 267–75.

Vogel, W. (1999). "Discoidin domain receptors: structural relations and functional implications." *Faseb J* 13(Suppl): S77–82.

Xin, et al., 1997 Direct Submission. GenBank Accession No. O54860.

Xin, X., R. Day, et al. (1998). "Identification of mouse CPX–2, a novel member of the metallocarboxypeptidase gene family: cDNA cloning, mRNA distribution, and protein expression and characterization." *DNA Cell Biol* 17(10): 897–909.

* cited by examiner

GCGGGGGGCAGGAAGGGGCGGGGGGCTCGGCGCACTCGGCAGGAAGAGACCGACCCGCC
ACCCGCCGTAGCCCGCGCGCCCCTGGCACTCAATCCCCGCCATGTGGGGGCTCCTGCTCG
CCCTGGCCGCCTTCGCGCCGGCCGTCGGCCCGGCTCTGGGGGCGCCCAGGAACTCGGTGC
TGGGCCTCGCGCAGCCCGGGACCACCAAGGTCCCAGGCTCGACCCCGGCCCTGCATAGCA
GCCCGGCACAGCCGCCGGCGGAGACAGCTAACGGGACCTCAGAACAGCATGTCCGGATT
CGAGTCATCAAGAAGAAAAAGGTCATTATGAAGAAGCGGAAGAAGCTAACTCTAACTCG
CCCCACCCCACTGGTGACTGCCGGGCCCCTTGTGACCCCACTCCAGCAGGGACCCTCGA
CCCCGCTGAGAAACAAGAAACAGGCTGTCCTCCTTTGGGTCTGGAGTCCCTGCGAGTTTC
AGATAGCCGGCTTGAGGCATCCAGCAGCCAGTCCTTTGGTCTTGGACCACACCGAGGACG
GCTCAACATTCAGTCAGGCCTGGAGGACGGCGATCTATATGATGGAGCCTGGTGTGCTGA
GGAGCAGGACGCCGATCCATGGTTTCAGGTGGACGCTGGGCACCCCACCCGCTTCTCGGG
TGTTATCACACAGGGCAGGAACTCTGTCTGGAGGTATGACTGGGTCACATCATACAAGGT
CCAGTTCAGCAATGACAGTCGGACCTGGTGGGAAGTAGGAACCACAGCAGTGGGATGG
ACGCAGTATTTCCTGCCAATTCAGACCCAGAAACTCCAGTGCTGAACCTCCTGCCGGAGC
CCCAGGTGGCCCGCTTCATTCGCCTGCTGCCCCAGACCTGGCTCCAGGGAGGCGCGCCTTG
CCTCCGGGCAGAGATCCTGGCCTGCCCAGTCTCAGACCCCAATGACCTATTCCTTGAGGCC
CCTGCGTCGGGATCCTCTGACCCTCTAGACTTTCAGCATCACAATTACAAGGCCATGAGGA
AGCTGATGAAGCAGGTACAAGAGCAATGCCCCAACATCACCCGCATCTACAGCATTGGGA
AGAGCTACCAGGGCCTGAAGCTGTATGTGATGGAAATGTCGGACAAGCCTGGGGAGCAT
GAGCTGGGGGAGCCTGAGGTGCGCTACGTGGCTGGCATGCATGGGAACGAGGCCCTGGG
GCGGGAGTTGCTTCTGCTCCTGATGCAGTTCCTGTGCCATGAGTTCCTGCGAGGGAACCCA
CGGGTGACCCGGCTGCTCTCTGAGATGCGCATTCACCTGCTGCCCTCCATGAACCCTGATG
GCTATGAGATCGCCTACCACCGGGGTTCAGAGCTGGTGGGCTGGGCCGAGGGCCGCTGGA
ACAACCAGAGCATCGATCTTAACCATAATTTTGCTGACCTCAACACACCACTGTGGGAAG
CACAGGACGATGGGAAGGTGCCCCACATCGTCCCCAACCATCACCTGCCATTGCCCACTT
ACTACACCCTGCCCAATGCCACCGTGGCTCCTGAAACGCGGGCAGTAATCAAGTGGATGA
AGCGGATCCCCTTTGTGCTAAGTGCCAACCTCCACGGGGGTGAGCTCGTGGTGTCCTACCC
ATTCGACATGACTCGCACCCCGTGGGCTGCCCGCGAGCTCACGCCCACACCAGATGATGC
TGTGTTTCGCTGGCTCAGCACTGTCTATGCTGGCAGTAATCTGGCCATGCAGGACACCAGC
CGCCGACCCTGCCACAGCCAGGACTTCTCCGTGCACGGCAACATCATCAACGGGCTGAC
TGGCACACGGTCCCCGGGAGCATGAATGACTTCAGCTACCTACACACCAACTGCTTTGAG
GTCACTGTGGAGCTGTCCTGTGACAAGTTCCCTCACGAGAATGAATTGCCCCAGGAGTGG
GAGAACAACAAAGACGCCCTCCTCACCTACCTGGAGCAGGTGCGCATGGGCATTGCAGGA
GTGGTGAGGGACAAGGACACGGAGCTTGGGATTGCTGACGCTGTCATTGCCGTGGATGGG
ATTAACCATGACGTGACCACGGCGTGGGGCGGGGATTATTGGCGTCTGCTGACCCCAGGG
GACTACATGGTGACTGCCAGTGCCGAGGGCTACCATTCAGTGACACGGAACTGTCGGGTC
ACCTTTGAAGAGGGCCCCTTCCCCTGCAATTTCGTGCTCACCAAGACTCCCAAACAGAGG
CTGCGCGAGCTGCTGGCAGCTGGGGCCAAGGTGCCCCGGACCTTCGCAGGCGCCTGGAG
CGGCTAAGGGGACAGAAGGATTGATACCTGCGGTTTAAGAGCCCTAGGGCAGGCTGGAC
CTGTCAAGACGGGAAGGGGAAGAGTAGAGAGGGAGGGACAAA

Fig. 1

MWGLLLALAAFAPAVGPALGAPRNSVLGLAQPGTTKVPGSTPALHSSPAQPPAETAN
GTSEQHVRIRVIKKKKVIMKKRKKLTLTRPTPLVTAGPLVTPTPAGTLDPAEKQETGC
PPLGLESLRVSDSRLEASSSQSFGLGPHRGRLNIQSGLEDGDLYDGAWCAEEQDA
DPWFQVDAGHPTRFSGVITQGRNSVWRYDWVTSYKVQFSNDSRTWWGSRNHSS
GMDAVFPANSDPETPVLNLLPEPQVARFIRLLPQTWLQGGAPCLRAEILACPVSD
PNDLFLEAPASGSSDPLDF*QHHNYKAMRKLMKQVQEQCPNITRIYSIGKSYQGLKLYVME*
*MSDKPGEHELGEPEORYEAGMHGNEALGRELLLLLMQFLCHEFLRGNPRVTRLLSEMRIH*
*LLPSMNPDGYEI*AYHRGSELVGWAEGRWNNQSIDLNHNFADLNTPLWEAODDGKVP
HIVPNHHLPLPTYYTLPNATVAPETRAVIKWMKRIPFVLSANLHGGELVVSYPFDMTR
TPWAARELTPTPDDAVFRWLSTVYAGSNLAMQDTSRRPCHSODFSVHGNIINGADW
HTVPGSMNDFSYLHTNCFEVTVELSCDKFPHENELPQEWENNKDALLTYLEQVRMGI
AGVVRDKDTELGIADAVIAVDGINHDVTTAWGGDYWRLLTPGDYMVTASAEGYHS
VTRNCRVTFEEGPFPCNFVLTKTPKQRLRELLAAGAKVPPDLRRRLERLRGQKD

Fig. 2

```
Q61281                    ..................................................
O88442                    MAPVRTASLLCGLLALLTLCPEGNPQTVLTDDEIEEFLEGFLSELETQSPPREDDVEVQP
Q14113                    ..................................................
O54860                    ..................................................
AL035460_GENSCAN_predicted_pep  ..................................................

Q61281                    ..................................................
O88442                    LPEPTQRPRKSKAGGKQRADVEVPPEKNKDKEKKGKKDKGPKATKPLEGSTRPTKKPKEK
Q14113                    ..................................................
O54860                    ..................................................
AL035460_GENSCAN_predicted_pep  ..................................................

Q61281                    ..................................................
O88442                    PPKATKKPKEKPPKATKKPKEKPPKATKKPKEKPPKATKRPSAGKKFSTVAPLETLDRLL
Q14113                    ..................................................
O54860                    ..................................................
AL035460_GENSCAN_predicted_pep  ..................................................

Q61281                    ..................................................
O88442                    PSPSNPSAQELPQKRDTPFPNAWQGQGEETQVEAKQPRPEPEEETEMPTLDYNDQIEKED
Q14113                    ..................................................
O54860                    ...........................................MARLGTAC
AL035460_GENSCAN_predicted_pep  ..................................................

Q61281                    ..................................................
O88442                    YEDFEYIRRQKQPRPTPSRRRLWPEREEKTEEPEERKEVEPPLKELLPPDYGDSYVIPN
Q14113                    ..................................................
O54860                    PALALAIALVAVALAGVRAQGAAFEEDYYSQELWRRGRYYGHPEPEPEPELFSPSMHED
AL035460_GENSCAN_predicted_pep  ..............MWGLLLALAAFAPAVGPALGAPRNSVLGLAQP......GTIKVPGS Q61281                    YDDLEYYFPHPPPQKPDVGQEVDEEKEEMKKPKEGSSPKEDTEDKWIVEKNKDHKGPRK
O88442                    YDDLEYYFPHPPPQKPDVGQEVDEEKEEMKKPKEGSSPKEDTEDKWIVEKNKDHKGPRK
Q14113                    ...MDYYFGPPPPQKPDAERQTDEEKEELKKPKEDSSPKE.ETDKWAVEKGKDHKEPRK
O54860                    LRVEEQEQRPHQQGHRTPKKAIKPKKAPKREKLVAEIPPPGKNSNRKGRRSKNLEKAAS
AL035460_GENSCAN_predicted_pep  TPALHSSPAQPPAETANGISEQHVRIRVIKKKKVIMKKRKK.LTLTRPTPLVTAGPLVTP Q61281                    ..........................................VQAGANEDDYK
O88442                    GEELEEEWAPVEKIKGPPTGMESHREEDNQIRASSMLRHGICAQRGRENIVQAGANEDDYK
Q14113                    GEELEEEWTPTEKVKGPPTGMESHREEDNQIRASSMLRHGICAQRGRENIVQAGADDDYK
O54860                    DDHGVPVAHEDVRESGPPLGIEITKEIDFQLHASISKRYGICABRGRENITQAGINENDFY
AL035460_GENSCAN_predicted_pep  TPAGTLEPAEKQETGCPPGLESLRVSDSRLEASSSQSFGLCPHRGRENTQSGLEDGBIK Q61281                    DGAWGAEDESQLQIEVDIRRIERIEIGVILGRDSSTHDDEVIIEEVGPSNDSQIWVMYK
O88442                    DGAWGAEDESQLQIEVDIRRIERIEIGVILGRDSSTHDDEVIIEEVGPSNDSQIWVMYK
Q14113                    DGAWGAEDDARLQIEVDIRRIERIEIGVILGRDSSTHDDEVIIEEVGPSNDSQIWVMYK
O54860                    DGAWGAGRNDLHQWIEVDARRLIKEIGVILGGRNSLWLSDAVSYKMVSNDSHIWTVK
AL035460_GENSCAN_predicted_pep  DGAWGAEEQDADPWFQVDAGHPIRFSGVILGGRNSVWRYDAVSYKYQFSNDSRIWGSR Q61281                    NGYE..EVIHFYGNVDKDTPVISELPEPVWAREFIRIVPLTAN..GSEGMRLEVLGGPVT.P
O88442                    NGYE..EVIHFYGNVDKDTPVISELPEPVWAREFIRIVPLTAN..GSEGMRLEVLGGPVT.P
Q14113                    NGYE..EVIHFYGNVDKDTPVISELPEPVWAREFIRIVPLTAN..GSEGMRLEVLGGSVA.
O54860                    NGSG..DVIEEGNSEKEIDVENEEPVMVARVIENPQSIFDNGSIGMREDVGGPLPD
AL035460_GENSCAN_predicted_pep  NHSSGMDAVEPANSDPETIVENLEEPQVAREFIRILPQTIILQGCAPCIRAEFACEASDP Q61281                    VVSYAYAQNEVVIEDSEDFRHESYKDMRQEMKAVNEEGPTTRLYSLGKSSRGLKEYAMEI
O88442                    VVSYAYAQNEVVIEDSEDFRHESYKDMRQEMKAVNEEGPTTRLYSLGKSSRGLKEYAMEI
Q14113                    VVSYAYAQNEVVAIDDEDFRHESYKDMRQEMKAVNEEGPTTRLYSLGKSSRGLKEYAMEI
O54860                    NNYYHRRNEMITEDEDKIENYKEMPQLMKVNEMGPNIRIDNICKSHQGLKVAVMEI
AL035460_GENSCAN_predicted_pep  NDLELEAPASGSSDPFDEQIENYKAMRELMKQVEQGCNITRLYSLGKSYQGLKLCVMMEM
```

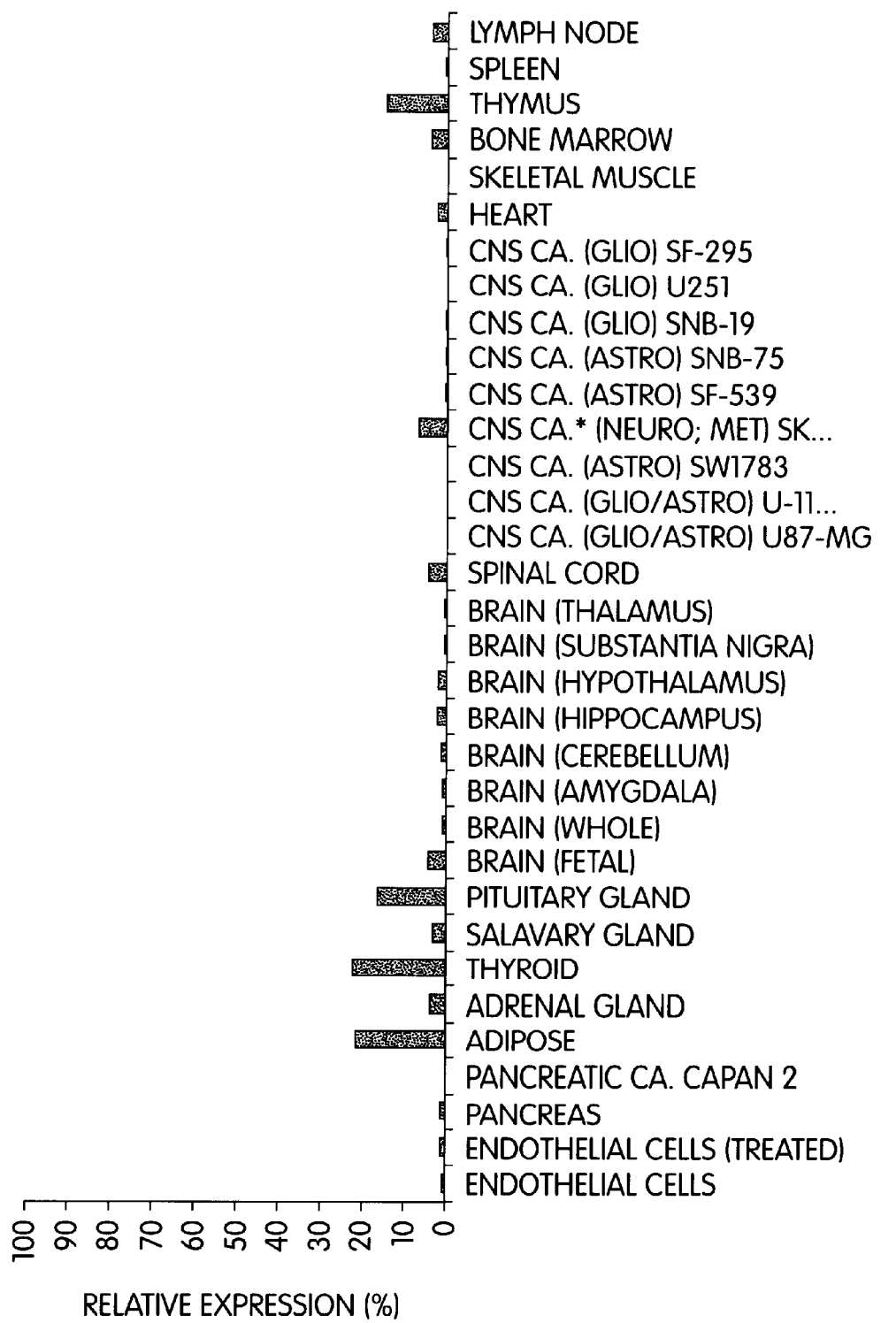

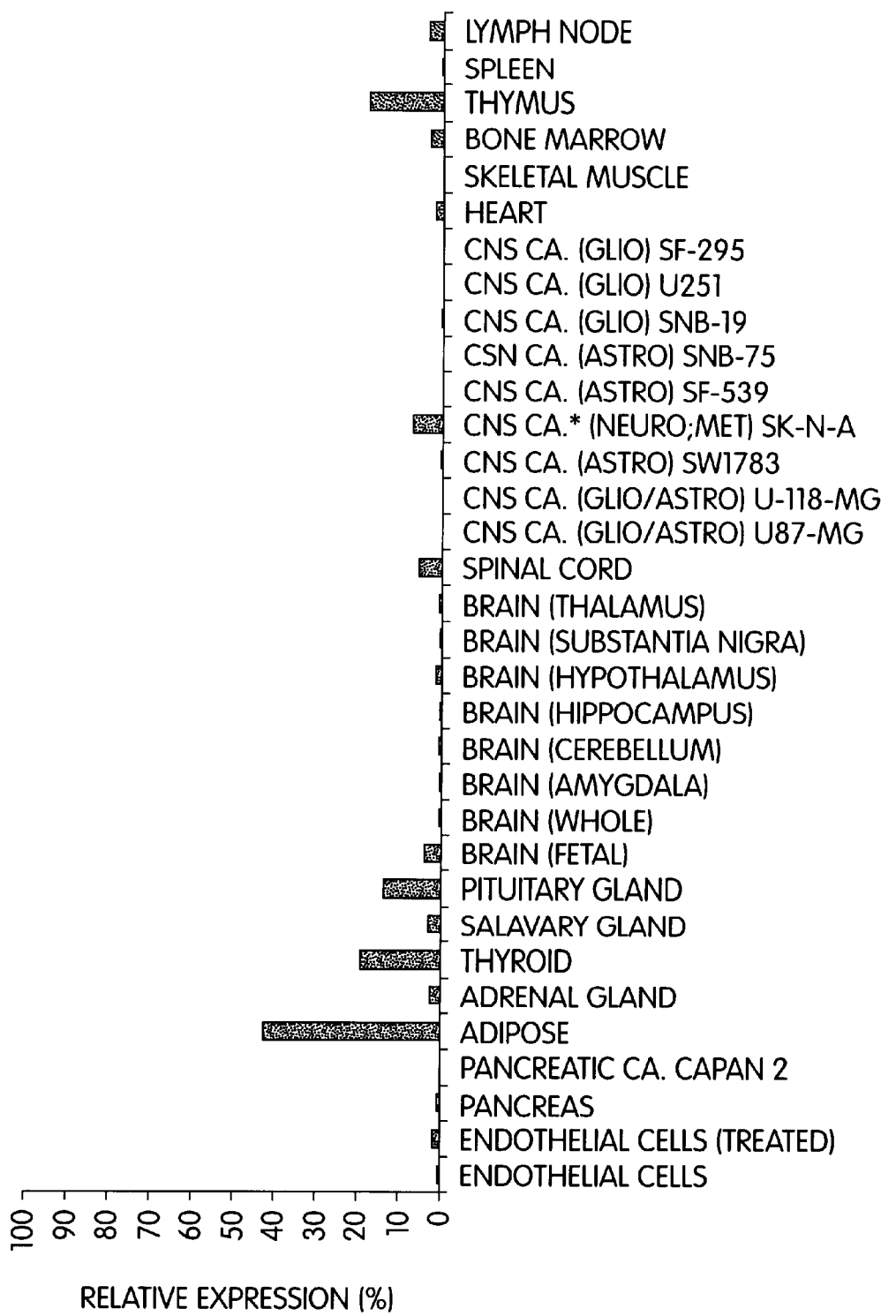

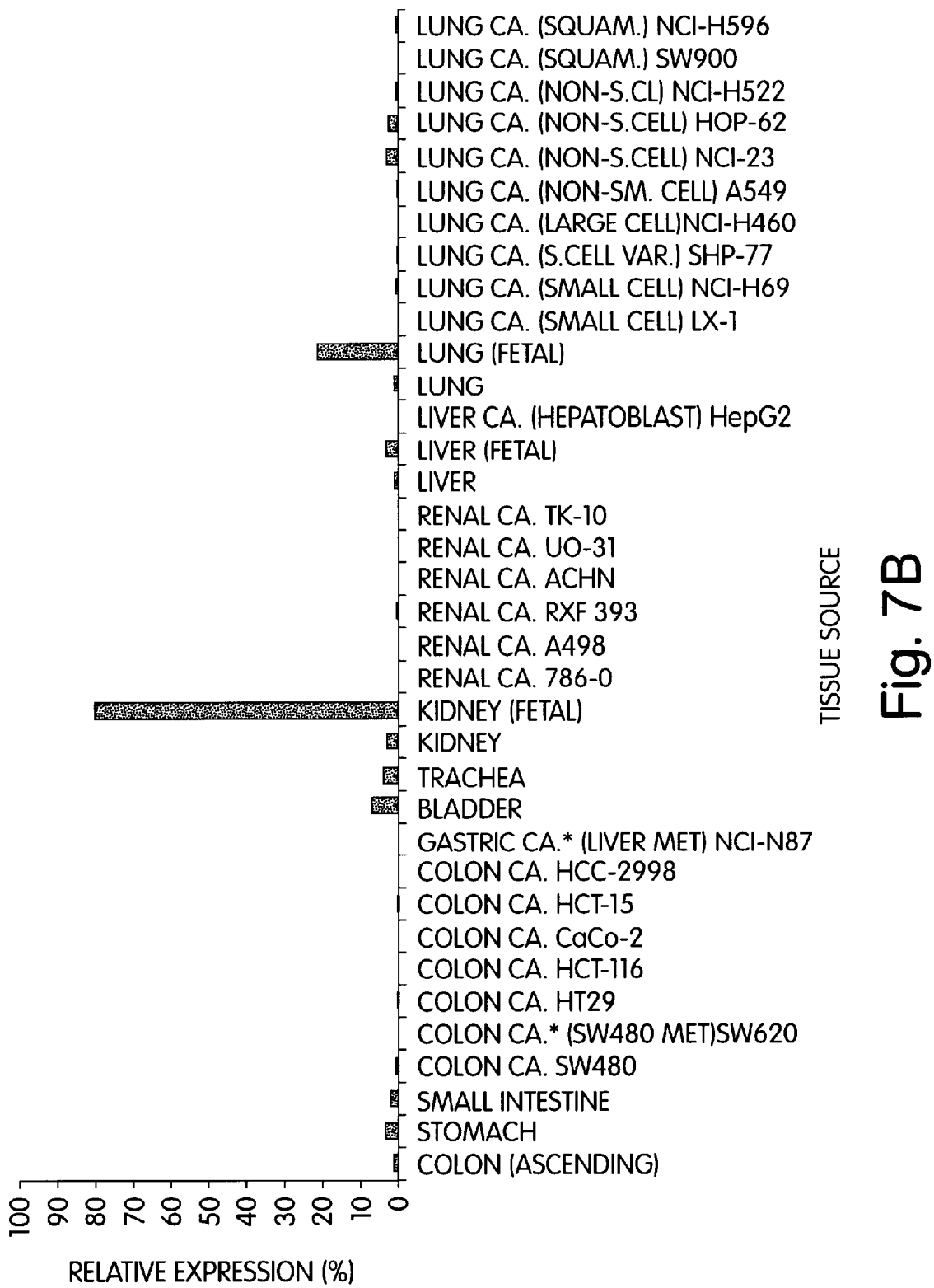

SEQUENCE LISTING

```
<160> NUMBER OF SEQ ID NOS:  32

<210> SEQ ID NO 1
<211> LENGTH: 2382
<212> TYPE: DNA
<213> ORGANISM: Homo sapiens

<400> SEQUENCE: 1 gcgggggca ggaaggggcg gggggctcgg cgcactcggc aggaagagac cgacccgcca      60
cccgccgtag cccgcgcgcc cctggcactc aatcccgcc atgtggggc tcctgctcgc     120 cctggccgcc ttcgcgccgg ccgtcggccc ggctctgggg gcgcccagga actcggtgct     180
gggcctcgcg cagcccggga ccaccaaggt cccaggctcg accccggccc tgcatagcag     240
cccggcacag ccgccggcgg agacagctaa cgggacctca gaacagcatg tccggattcg     300
agtcatcaag aagaaaaagg tcattatgaa gaagcggaag aagctaactc taactcgccc     360 cacccactg gtgactgccg ggccccttgt gaccccact ccagcaggga ccctcgaccc     420
cgctgagaaa caagaaacag gctgtcctcc tttgggtctg gagtccctgc gagtttcaga     480
tagccggctt gaggcatcca gcagccagtc ctttggtctt ggaccacacc gaggacggct     540
caacattcag tcaggcctgg aggacggcga tctatatgat ggagcctggt gtgctgagga     600
gcaggacgcc gatccatggt ttcaggtgga cgctgggcac cccacccgct tctcgggtgt     660
tatcacacag ggcaggaact ctgtctggag gtatgactgg gtcacatcat acaaggtcca     720
gttcagcaat gacagtcgga cctggtgggg aagtaggaac cacagcagtg ggatggacgc     780
agtatttcct gccaattcag acccagaaac tccagtgctg aacctcctgc cggagcccca     840
ggtggcccgc ttcattcgcc tgctgcccca gacctggctc cagggaggcg cgccttgcct     900
ccgggcagag atcctggcct gcccagtctc agaccccaat gacctattcc ttgaggcccc     960
tgcgtcggga tcctctgacc ctctagactt tcagcatcac aattacaagg ccatgaggaa    1020
gctgatgaag caggtacaag agcaatgccc caacatcacc cgcatctaca gcattgggaa    1080
gagctaccag ggcctgaagc tgtatgtgat ggaaatgtcg gacaagcctg gggagcatga    1140
gctgggggag cctgaggtgc gctacgtggc tggcatgcat gggaacgagg ccctggggcg    1200
ggagttgctt ctgctcctga tgcagttcct gtgccatgag ttcctgcgag ggaacccacg    1260
ggtgacccgg ctgctctctg agatgcgcat tcacctgctg ccctccatga accctgatgg    1320
```

-continued

```
ctatgagatc gcctaccacc ggggttcaga gctggtgggc tgggccgagg ccgctggaa      1380 caaccagagc atcgatctta accataattt tgctgacctc aacacaccac tgtgggaagc      1440
acaggacgat gggaaggtgc cccacatcgt ccccaaccat cacctgccat tgcccactta      1500
ctacaccctg cccaatgcca ccgtggctcc tgaaacgcgg gcagtaatca agtggatgaa      1560
gcggatcccc tttgtgctaa gtccaacctc cacgggggt gagctcgtgg tgtcctaccc       1620
attcgacatg actcgcaccc cgtgggctgc ccgcgagctc acgcccacac agatgatgc       1680 tgtgtttcgc tggctcagca ctgtctatgc tggcagtaat ctggccatgc aggacaccag      1740
ccgccgaccc tgccacagcc aggacttctc cgtgcacggc aacatcatca cgggggctga     1800
ctggcacacg gtccccggga gcatgaatga cttcagctac ctacacacca actgctttga     1860
ggtcactgtg gagctgtcct gtgacaagtt ccctcacgag aatgaattgc cccaggagtg     1920
ggagaacaac aaagacgccc tcctcaccta cctggagcag gtgcgcatgg gcattgcagg     1980
agtggtgagg gacaaggaca cggagcttgg gattgctgac gctgtcattg ccgtggatgg     2040
gattaaccat gacgtgacca cggcgtgggg cggggattat tggcgtctgc tgaccccagg     2100
ggactacatg gtgactgcca gtgccgaggg ctaccattca gtgacacgga actgtcgggt     2160 caccttttgaa gagggcccct tcccctgcaa tttcgtgctc accaagactc ccaaacagag     2220
gctgcgcgag ctgctggcag ctggggccaa ggtgccccg gaccttcgca ggcgcctgga      2280
gcggctaagg ggacagaagg attgatacct gcggtttaag agccctaggg caggctggac     2340
ctgtcaagac gggaagggga agagtagaga gggagggaca aa                        2382
```

<210> SEQ ID NO 2
<211> LENGTH: 734
<212> TYPE: PRT
<213> ORGANISM: Homo sapiens

<400> SEQUENCE: 2

```
Met Trp Gly Leu Leu Ala Leu Ala Ala Phe Ala Pro Ala Val Gly
  1               5                  10                  15

Pro Ala Leu Gly Ala Pro Arg Asn Ser Val Leu Gly Leu Ala Gln Pro
                 20                  25                  30

Gly Thr Thr Lys Val Pro Gly Ser Thr Pro Ala Leu His Ser Ser Pro
             35                  40                  45

Ala Gln Pro Pro Ala Glu Thr Ala Asn Gly Thr Ser Glu Gln His Val
         50                  55                  60

Arg Ile Arg Val Ile Lys Lys Lys Val Ile Met Lys Lys Arg Lys
 65                  70                  75                  80

Lys Leu Thr Leu Thr Arg Pro Thr Pro Leu Val Thr Ala Gly Pro Leu
                 85                  90                  95

Val Thr Pro Thr Pro Ala Gly Thr Leu Asp Pro Ala Glu Lys Gln Glu
            100                 105                 110

Thr Gly Cys Pro Pro Leu Gly Leu Glu Ser Leu Arg Val Ser Asp Ser
            115                 120                 125

Arg Leu Glu Ala Ser Ser Ser Gln Ser Phe Gly Leu Gly Pro His Arg
        130                 135                 140

Gly Arg Leu Asn Ile Gln Ser Gly Leu Glu Asp Gly Asp Leu Tyr Asp
145                 150                 155                 160

Gly Ala Trp Cys Ala Glu Glu Gln Asp Ala Asp Pro Trp Phe Gln Val
                165                 170                 175

Asp Ala Gly His Pro Thr Arg Phe Ser Gly Val Ile Thr Gln Gly Arg
```

-continued

```
                180                 185                 190
Asn Ser Val Trp Arg Tyr Asp Trp Val Thr Ser Tyr Lys Val Gln Phe
            195                 200                 205
Ser Asn Asp Ser Arg Thr Trp Trp Gly Ser Arg Asn His Ser Ser Gly
            210                 215                 220
Met Asp Ala Val Phe Pro Ala Asn Ser Asp Pro Glu Thr Pro Val Leu
225                 230                 235                 240
Asn Leu Leu Pro Glu Pro Gln Val Ala Arg Phe Ile Arg Leu Leu Pro
                245                 250                 255
Gln Thr Trp Leu Gln Gly Gly Ala Pro Cys Leu Arg Ala Glu Ile Leu
            260                 265                 270
Ala Cys Pro Val Ser Asp Pro Asn Asp Leu Phe Leu Glu Ala Pro Ala
            275                 280                 285
Ser Gly Ser Ser Asp Pro Leu Asp Phe Gln His His Asn Tyr Lys Ala
            290                 295                 300
Met Arg Lys Leu Met Lys Gln Val Gln Glu Gln Cys Pro Asn Ile Thr
305                 310                 315                 320
Arg Ile Tyr Ser Ile Gly Lys Ser Tyr Gln Gly Leu Lys Leu Tyr Val
                325                 330                 335
Met Glu Met Ser Asp Lys Pro Gly Glu His Glu Leu Gly Glu Pro Glu
            340                 345                 350
Val Arg Tyr Val Ala Gly Met His Gly Asn Glu Ala Leu Gly Arg Glu
            355                 360                 365
Leu Leu Leu Leu Leu Met Gln Phe Leu Cys His Glu Phe Leu Arg Gly
            370                 375                 380
Asn Pro Arg Val Thr Arg Leu Leu Ser Glu Met Arg Ile His Leu Leu
385                 390                 395                 400
Pro Ser Met Asn Pro Asp Gly Tyr Glu Ile Ala Tyr His Arg Gly Ser
                405                 410                 415
Glu Leu Val Gly Trp Ala Glu Gly Arg Trp Asn Asn Gln Ser Ile Asp
            420                 425                 430
Leu Asn His Asn Phe Ala Asp Leu Asn Thr Pro Leu Trp Glu Ala Gln
            435                 440                 445
Asp Asp Gly Lys Val Pro His Ile Val Pro Asn His His Leu Pro Leu
450                 455                 460
Pro Thr Tyr Tyr Thr Leu Pro Asn Ala Thr Val Ala Pro Glu Thr Arg
465                 470                 475                 480
Ala Val Ile Lys Trp Met Lys Arg Ile Pro Phe Val Leu Ser Ala Asn
                485                 490                 495
Leu His Gly Gly Glu Leu Val Val Ser Tyr Pro Phe Asp Met Thr Arg
            500                 505                 510
Thr Pro Trp Ala Ala Arg Glu Leu Thr Pro Thr Pro Asp Asp Ala Val
            515                 520                 525
Phe Arg Trp Leu Ser Thr Val Tyr Ala Gly Ser Asn Leu Ala Met Gln
            530                 535                 540
Asp Thr Ser Arg Arg Pro Cys His Ser Gln Asp Phe Ser Val His Gly
545                 550                 555                 560
Asn Ile Ile Asn Gly Ala Asp Trp His Thr Val Pro Gly Ser Met Asn
                565                 570                 575
Asp Phe Ser Tyr Leu His Thr Asn Cys Phe Glu Val Thr Val Glu Leu
            580                 585                 590
Ser Cys Asp Lys Phe Pro His Glu Asn Glu Leu Pro Gln Glu Trp Glu
            595                 600                 605
```

```
Asn Asn Lys Asp Ala Leu Leu Thr Tyr Leu Glu Gln Val Arg Met Gly
    610                 615                 620

Ile Ala Gly Val Val Arg Asp Lys Asp Thr Glu Leu Gly Ile Ala Asp
625                 630                 635                 640

Ala Val Ile Ala Val Asp Gly Ile Asn His Asp Val Thr Thr Ala Trp
                645                 650                 655

Gly Gly Asp Tyr Trp Arg Leu Leu Thr Pro Gly Asp Tyr Met Val Thr
            660                 665                 670

Ala Ser Ala Glu Gly Tyr His Ser Val Thr Arg Asn Cys Arg Val Thr
            675                 680                 685

Phe Glu Glu Gly Pro Phe Pro Cys Asn Phe Val Leu Thr Lys Thr Pro
    690                 695                 700

Lys Gln Arg Leu Arg Glu Leu Leu Ala Ala Gly Ala Lys Val Pro Pro
705                 710                 715                 720

Asp Leu Arg Arg Arg Leu Glu Arg Leu Arg Gly Gln Lys Asp
                725                 730

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 3
ctcgtcagat ctgcgcccag gaactcggtg ctgggcctcg                           40

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 4
ctcgtcctcg agatccttct gtccccttag ccgctcc                              37

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 5
agccggcttg aggcatccag c                                               21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 6
gctggatgcc tcaagccggc t                                               21

<210> SEQ ID NO 7
```

```
<211> LENGTH: 21
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 7
ccagaaactc cagtgctgaa c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 8
gttcagcact ggagtttctg g                                              21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 9
caagcctggg gagcatgagc tg                                             22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 10
cagctcatgc tccccaggct tg                                             22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 11
caggacgatg ggaaggtgcc c                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 12
gggcaccttc ccatcgtcct g                                              21

<210> SEQ ID NO 13
<211> LENGTH: 21
```

```
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 13
agcatgaatg acttcagcta c                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 14
gtagctgaag tcattcatgc t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 15
gagcttggga ttgctgacgc t                                              21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 16
gcgtcagcaa tcccaagctc                                                20

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 17
ctcgtcctcg agggtaagcc tatccctaac                                     30

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 18
ctcgtcgggc ccctgatcag cgggtttaaa c                                   31

<210> SEQ ID NO 19
<211> LENGTH: 21
<212> TYPE: DNA
```

```
<213> ORGANISM: Artificial Sequence
<220> FEATURE:
<223> OTHER INFORMATION: Description of Artificial Sequence: Chemically
      Synthesized

<400> SEQUENCE: 19
gtctggagtc cctgcgagtt t                                          21

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 20
cggtgtggtc caagaccaa                                             19

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 21
cttgaggcat ccagcagcca gtcc                                       24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 22
gagtccctgc gagtttcaga tag                                        23

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 23
gtcctcggtg tggtccaaga                                            20

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 24
tgaggcatcc agcagccagt ccttt                                      25

<210> SEQ ID NO 25
<211> LENGTH: 23
<212> TYPE: DNA
<213> ORGANISM: Artificial Sequence
```

```
<220> FEATURE:
<223> OTHER INFORMATION: Description of Artificial Sequence: Chemically
      Synthesized

<400> SEQUENCE: 25
gtgctgctgc tctacaataa cca                                             23

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 26
gtttctgcag ctgggccat                                                  19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Chemically
      Synthesized

<400> SEQUENCE: 27
tggaccggtg cgccttcgat                                                 20

<210> SEQ ID NO 28
<211> LENGTH: 719
<212> TYPE: PRT
<213> ORGANISM: Mus musculus

<400> SEQUENCE: 28
```

Met Gln Ala Gly Ala Asn Glu Asp Asp Tyr Tyr Asp Gly Ala Trp Cys
 1               5                  10                  15

Ala Glu Asp Glu Ser Gln Thr Gln Trp Ile Glu Val Asp Thr Arg Arg
                20                  25                  30

Thr Thr Arg Phe Thr Gly Val Ile Thr Gln Gly Arg Asp Ser Ser Ile
            35                  40                  45

His Asp Asp Phe Val Thr Thr Phe Phe Val Gly Phe Ser Asn Asp Ser
        50                  55                  60

Gln Thr Trp Val Met Tyr Thr Asn Gly Tyr Glu Glu Met Thr Phe Tyr
65                  70                  75                  80

Gly Asn Val Asp Lys Asp Thr Pro Val Leu Ser Glu Leu Pro Glu Pro
                85                  90                  95

Val Val Ala Arg Phe Ile Arg Ile Tyr Pro Leu Thr Trp Asn Gly Ser
                100                 105                 110

Leu Cys Met Arg Leu Glu Val Leu Gly Cys Pro Val Thr Pro Val Tyr
            115                 120                 125

Ser Tyr Tyr Ala Gln Asn Glu Val Val Thr Thr Asp Ser Leu Asp Phe
        130                 135                 140

Arg His His Ser Tyr Lys Asp Met Arg Gln Leu Met Lys Ala Val Asn
145                 150                 155                 160

Glu Glu Cys Pro Thr Ile Thr Arg Thr Tyr Ser Leu Gly Lys Ser Ser
                165                 170                 175

Arg Gly Leu Lys Ile Tyr Ala Met Glu Ile Ser Asp Asn Pro Gly Asp
                180                 185                 190

His Glu Leu Gly Glu Pro Glu Phe Arg Tyr Thr Ala Gly Ile His Gly

-continued

```
            195                 200                 205
Asn Glu Val Leu Gly Arg Glu Leu Leu Leu Leu Met Gln Tyr Leu
        210                 215                 220
Cys Gln Glu Tyr Arg Asp Gly Asn Pro Arg Val Arg Asn Leu Val Gln
225                 230                 235                 240
Asp Thr Arg Ile His Leu Val Pro Ser Leu Asn Pro Asp Gly Tyr Glu
                245                 250                 255
Val Ala Ala Gln Met Gly Ser Glu Phe Gly Asn Trp Ala Leu Gly Leu
            260                 265                 270
Trp Thr Glu Glu Gly Phe Asp Ile Phe Glu Asp Phe Pro Asp Leu Asn
        275                 280                 285
Ser Val Leu Trp Ala Ala Glu Glu Lys Lys Trp Val Pro Tyr Arg Val
    290                 295                 300
Pro Asn Asn Leu Pro Ile Pro Glu Arg Tyr Leu Ser Pro Asp Ala
305                 310                 315                 320
Thr Val Ser Thr Glu Val Arg Ala Ile Ile Ser Trp Met Glu Lys Asn
                325                 330                 335
Pro Phe Val Leu Gly Ala Asn Leu Asn Gly Gly Glu Arg Leu Val Ser
            340                 345                 350
Tyr Pro Tyr Asp Met Ala Arg Thr Pro Ser Gln Glu Gln Leu Leu Ala
        355                 360                 365
Glu Ala Leu Ala Ala Ala Arg Gly Glu Asp Asp Gly Val Ser Glu
370                 375                 380
Ala Gln Glu Thr Pro Asp His Ala Ile Phe Arg Trp Leu Ala Ile Ser
385                 390                 395                 400
Phe Ala Ser Ala His Leu Thr Met Thr Glu Pro Tyr Arg Gly Gly Cys
                405                 410                 415
Gln Ala Gln Asp Tyr Thr Ser Gly Met Gly Ile Val Asn Gly Ala Lys
            420                 425                 430
Trp Asn Pro Arg Ser Gly Thr Phe Asn Asp Phe Ser Tyr Leu His Thr
        435                 440                 445
Asn Cys Leu Glu Leu Ser Val Tyr Leu Gly Cys Asp Lys Phe Pro His
    450                 455                 460
Glu Ser Glu Leu Pro Arg Glu Trp Glu Asn Asn Lys Glu Ala Leu Leu
465                 470                 475                 480
Thr Phe Met Glu Gln Val His Arg Gly Ile Lys Gly Val Val Thr Asp
                485                 490                 495
Glu Gln Gly Ile Pro Ile Ala Asn Ala Thr Ile Ser Val Ser Gly Ile
            500                 505                 510
Asn His Gly Val Lys Thr Ala Ser Gly Gly Asp Tyr Trp Arg Ile Leu
        515                 520                 525
Asn Pro Gly Glu Tyr Arg Val Thr Ala His Ala Glu Gly Tyr Thr Ser
    530                 535                 540
Ser Ala Lys Ile Cys Asn Val Asp Tyr Asp Ile Gly Ala Thr Gln Cys
545                 550                 555                 560
Asn Phe Ile Leu Ala Arg Ser Asn Trp Lys Arg Ile Arg Glu Ile Leu
                565                 570                 575
Ala Met Asn Gly Asn Arg Pro Ile Leu Arg Val Asp Pro Ser Arg Pro
            580                 585                 590
Met Thr Pro Gln Gln Arg Arg Met Gln Gln Arg Leu Gln Tyr Arg
        595                 600                 605
Leu Arg Met Arg Glu Gln Met Arg Leu Arg Arg Leu Asn Ser Thr Ala
    610                 615                 620
```

-continued

Gly Pro Ala Thr Ser Pro Thr Pro Ala Leu Met Pro Pro Ser Pro
625                 630                 635                 640

Thr Pro Ala Ile Thr Leu Arg Pro Trp Glu Val Leu Pro Thr Thr Thr
            645                 650                 655

Ala Gly Trp Glu Glu Ser Glu Thr Glu Thr Tyr Thr Glu Val Val Thr
        660                 665                 670

Glu Phe Glu Thr Glu Tyr Gly Thr Asp Leu Glu Val Glu Glu Ile Glu
            675                 680                 685

Glu Glu Glu Glu Glu Glu Glu Glu Met Asp Thr Gly Leu Thr Phe
        690                 695                 700

Pro Leu Thr Thr Val Glu Thr Tyr Thr Val Asn Phe Gly Asp Phe
705                 710                 715

<210> SEQ ID NO 29
<211> LENGTH: 845
<212> TYPE: PRT
<213> ORGANISM: Homo sapiens

<400> SEQUENCE: 29

Met Asp Tyr Tyr Phe Gly Pro Pro Pro Gln Lys Pro Asp Ala Glu
1               5                   10                  15

Arg Gln Thr Asp Glu Glu Lys Glu Glu Leu Lys Lys Pro Lys Lys Glu
            20                  25                  30

Asp Ser Ser Pro Lys Glu Glu Thr Asp Lys Trp Ala Val Glu Lys Gly
        35                  40                  45

Lys Asp His Lys Glu Pro Arg Lys Gly Glu Glu Leu Glu Glu Glu Trp
    50                  55                  60

Thr Pro Thr Glu Lys Val Lys Cys Pro Pro Ile Gly Met Glu Ser His
65                  70                  75                  80

Arg Ile Glu Asp Asn Gln Ile Arg Ala Ser Ser Met Leu Arg His Gly
                85                  90                  95

Leu Gly Ala Gln Arg Gly Arg Leu Asn Met Gln Thr Gly Ala Thr Glu
            100                 105                 110

Asp Asp Tyr Tyr Asp Gly Ala Trp Cys Ala Glu Asp Asp Ala Arg Thr
        115                 120                 125

Gln Trp Ile Glu Val Asp Thr Arg Arg Thr Thr Arg Phe Thr Gly Val
    130                 135                 140

Ile Thr Gln Gly Arg Asp Ser Ser Ile His Asp Asp Phe Val Thr Thr
145                 150                 155                 160

Phe Phe Val Gly Phe Ser Asn Asp Ser Gln Thr Trp Val Met Tyr Thr
                165                 170                 175

Asn Gly Tyr Glu Glu Met Thr Phe His Gly Asn Val Asp Lys Asp Thr
            180                 185                 190

Pro Val Leu Ser Glu Leu Pro Glu Pro Val Val Ala Arg Phe Ile Arg
        195                 200                 205

Ile Tyr Pro Leu Thr Trp Asn Gly Ser Leu Cys Met Arg Leu Glu Val
    210                 215                 220

Leu Gly Cys Ser Val Ala Pro Val Tyr Ser Tyr Tyr Ala Gln Asn Glu
225                 230                 235                 240

Val Val Ala Thr Asp Asp Leu Asp Phe Arg His His Ser Tyr Lys Asp
                245                 250                 255

Met Arg Gln Leu Met Lys Val Val Asn Glu Glu Cys Pro Thr Ile Thr
            260                 265                 270

Arg Thr Tyr Ser Leu Gly Lys Ser Ser Arg Gly Leu Lys Ile Tyr Ala

```
             275                 280                 285
Met Glu Ile Ser Asp Asn Pro Gly Glu His Glu Leu Gly Glu Pro Glu
290                 295                 300

Phe Arg Tyr Thr Ala Gly Ile His Gly Asn Glu Val Leu Gly Arg Glu
305                 310                 315                 320

Leu Leu Leu Leu Leu Met Gln Tyr Leu Cys Arg Glu Tyr Arg Asp Gly
                325                 330                 335

Asn Pro Arg Val Arg Ser Leu Val Gln Asp Thr Arg Ile His Leu Val
            340                 345                 350

Pro Ser Leu Asn Pro Asp Gly Tyr Glu Val Ala Ala Gln Met Gly Ser
            355                 360                 365

Glu Phe Gly Asn Trp Ala Leu Gly Leu Trp Thr Glu Gly Phe Asp
        370                 375                 380

Ile Phe Glu Asp Phe Pro Asp Leu Asn Ser Val Leu Trp Gly Ala Glu
385                 390                 395                 400

Glu Arg Lys Trp Val Pro Tyr Arg Val Pro Asn Asn Leu Pro Ile
                405                 410                 415

Pro Glu Arg Tyr Leu Ser Pro Asp Ala Thr Val Ser Thr Glu Val Arg
            420                 425                 430

Ala Ile Ile Ala Trp Met Glu Lys Asn Pro Phe Val Leu Gly Ala Asn
            435                 440                 445

Leu Asn Gly Gly Glu Arg Leu Val Ser Tyr Pro Tyr Asp Met Ala Arg
450                 455                 460

Thr Pro Thr Gln Glu Gln Leu Leu Ala Ala Ala Met Ala Ala Ala Arg
465                 470                 475                 480

Gly Glu Asp Glu Asp Glu Val Ser Glu Ala Gln Glu Thr Pro Asp His
                485                 490                 495

Ala Ile Phe Arg Trp Leu Ala Ile Ser Phe Ala Ser Ala His Leu Thr
            500                 505                 510

Leu Thr Glu Pro Tyr Arg Gly Gly Cys Gln Ala Gln Asp Tyr Thr Gly
            515                 520                 525

Gly Met Gly Ile Val Asn Gly Ala Lys Trp Asn Pro Arg Thr Gly Thr
530                 535                 540

Ile Asn Asp Phe Ser Tyr Leu His Thr Asn Cys Leu Glu Leu Ser Phe
545                 550                 555                 560

Tyr Leu Gly Cys Asp Lys Phe Pro His Glu Ser Glu Leu Pro Arg Glu
                565                 570                 575

Trp Glu Asn Asn Lys Glu Ala Leu Leu Thr Phe Met Glu Gln Val His
                580                 585                 590

Arg Gly Ile Lys Gly Val Val Thr Asp Glu Gln Gly Ile Pro Ile Ala
            595                 600                 605

Asn Ala Thr Ile Ser Val Ser Gly Ile Asn His Gly Val Lys Thr Ala
610                 615                 620

Ser Gly Gly Asp Tyr Trp Arg Ile Leu Asn Pro Gly Glu Tyr Arg Val
625                 630                 635                 640

Thr Ala His Ala Glu Gly Tyr Thr Pro Ser Ala Lys Thr Cys Asn Val
                645                 650                 655

Asp Tyr Asp Ile Gly Ala Thr Gln Cys Asn Phe Ile Leu Ala Arg Ser
            660                 665                 670

Asn Trp Lys Arg Ile Arg Glu Ile Met Ala Met Asn Gly Asn Arg Pro
            675                 680                 685

Ile Pro His Ile Asp Pro Ser Arg Pro Met Thr Pro Gln Gln Arg Arg
690                 695                 700
```

Leu Gln Gln Arg Arg Leu Gln His Arg Leu Arg Leu Arg Ala Gln Met
705                 710                 715                 720

Arg Leu Arg Arg Leu Asn Ala Thr Thr Thr Leu Gly Pro His Thr Val
            725                 730                 735

Pro Pro Thr Leu Pro Pro Ala Pro Ala Thr Thr Leu Ser Thr Thr Ile
            740                 745                 750

Glu Pro Trp Gly Leu Ile Pro Pro Thr Thr Ala Gly Trp Glu Glu Ser
            755                 760                 765

Glu Thr Glu Thr Tyr Thr Glu Val Val Thr Glu Phe Gly Thr Glu Val
770                 775                 780

Glu Pro Glu Phe Gly Thr Lys Val Glu Pro Glu Phe Glu Thr Gln Leu
785                 790                 795                 800

Glu Pro Glu Phe Glu Thr Gln Leu Glu Pro Glu Phe Glu Glu Glu Glu
            805                 810                 815

Glu Glu Glu Lys Glu Glu Glu Ile Ala Thr Gly Gln Ala Phe Pro Phe
            820                 825                 830

Thr Thr Val Glu Thr Tyr Thr Val Asn Phe Gly Asp Phe
            835                 840                 845

<210> SEQ ID NO 30
<211> LENGTH: 1128
<212> TYPE: PRT
<213> ORGANISM: Mus musculus

<400> SEQUENCE: 30

Met Ala Pro Val Arg Thr Ala Ser Leu Leu Cys Gly Leu Leu Ala Leu
1               5                   10                  15

Leu Thr Leu Cys Pro Glu Gly Asn Pro Gln Thr Val Leu Thr Asp Asp
            20                  25                  30

Glu Ile Glu Glu Phe Leu Glu Gly Phe Leu Ser Glu Leu Glu Thr Gln
        35                  40                  45

Ser Pro Pro Arg Glu Asp Asp Val Glu Val Gln Pro Leu Pro Glu Pro
    50                  55                  60

Thr Gln Arg Pro Arg Lys Ser Lys Ala Gly Gly Lys Gln Arg Ala Asp
65                  70                  75                  80

Val Glu Val Pro Pro Glu Lys Asn Lys Asp Lys Glu Lys Lys Gly Lys
                85                  90                  95

Lys Asp Lys Gly Pro Lys Ala Thr Lys Pro Leu Glu Gly Ser Thr Arg
            100                 105                 110

Pro Thr Lys Lys Pro Lys Glu Lys Pro Pro Lys Ala Thr Lys Lys Pro
            115                 120                 125

Lys Glu Lys Pro Pro Lys Ala Thr Lys Lys Pro Lys Glu Lys Pro Pro
            130                 135                 140

Lys Ala Thr Lys Lys Pro Lys Glu Lys Pro Pro Lys Ala Thr Lys Arg
145                 150                 155                 160

Pro Ser Ala Gly Lys Lys Phe Ser Thr Val Ala Pro Leu Glu Thr Leu
            165                 170                 175

Asp Arg Leu Leu Pro Ser Pro Ser Asn Pro Ser Ala Gln Glu Leu Pro
            180                 185                 190

Gln Lys Arg Asp Thr Pro Phe Pro Asn Ala Trp Gln Gly Gln Gly Glu
            195                 200                 205

Glu Thr Gln Val Glu Ala Lys Gln Pro Arg Pro Glu Pro Glu Glu Glu
            210                 215                 220

Thr Glu Met Pro Thr Leu Asp Tyr Asn Asp Gln Ile Glu Lys Glu Asp

```
225                 230                 235                 240

Tyr Glu Asp Phe Glu Tyr Ile Arg Arg Gln Lys Gln Pro Arg Pro Thr
                245                 250                 255

Pro Ser Arg Arg Arg Leu Trp Pro Glu Arg Pro Glu Glu Lys Thr Glu
                260                 265                 270

Glu Pro Glu Glu Arg Lys Glu Val Glu Pro Pro Leu Lys Pro Leu Leu
            275                 280                 285

Pro Pro Asp Tyr Gly Asp Ser Tyr Val Ile Pro Asn Tyr Asp Asp Leu
        290                 295                 300

Asp Tyr Tyr Phe Pro His Pro Pro Gln Lys Pro Asp Val Gly Gln
305                 310                 315                 320

Glu Val Asp Glu Glu Lys Glu Glu Met Lys Lys Pro Lys Lys Glu Gly
                325                 330                 335

Ser Ser Pro Lys Glu Asp Thr Glu Asp Lys Trp Thr Val Glu Lys Asn
            340                 345                 350

Lys Asp His Lys Gly Pro Arg Lys Gly Glu Glu Leu Glu Glu Glu Trp
        355                 360                 365

Ala Pro Val Glu Lys Ile Lys Cys Pro Pro Ile Gly Met Glu Ser His
    370                 375                 380

Arg Ile Glu Asp Asn Gln Ile Arg Ala Ser Ser Met Leu Arg His Gly
385                 390                 395                 400

Leu Gly Ala Gln Arg Gly Arg Leu Asn Met Gln Ala Gly Ala Asn Glu
                405                 410                 415

Asp Asp Tyr Tyr Asp Gly Ala Trp Cys Ala Glu Asp Glu Ser Gln Thr
            420                 425                 430

Gln Trp Ile Glu Val Asp Thr Arg Arg Thr Thr Arg Phe Thr Gly Val
        435                 440                 445

Ile Thr Gln Gly Arg Asp Ser Ser Ile His Asp Asp Phe Val Thr Thr
    450                 455                 460

Phe Phe Val Gly Phe Ser Asn Asp Ser Gln Thr Trp Val Met Tyr Thr
465                 470                 475                 480

Asn Gly Tyr Glu Glu Met Thr Phe Tyr Gly Asn Val Asp Lys Asp Thr
                485                 490                 495

Pro Val Leu Ser Glu Leu Pro Glu Pro Val Val Ala Arg Phe Ile Arg
            500                 505                 510

Ile Tyr Pro Leu Thr Trp Asn Gly Ser Leu Cys Met Arg Leu Glu Val
        515                 520                 525

Leu Gly Cys Pro Val Thr Pro Val Tyr Ser Tyr Tyr Ala Gln Asn Glu
    530                 535                 540

Val Val Thr Thr Asp Ser Leu Asp Phe Arg His His Ser Tyr Lys Asp
545                 550                 555                 560

Met Arg Gln Leu Met Lys Ala Val Asn Glu Glu Cys Pro Thr Ile Thr
                565                 570                 575

Arg Thr Tyr Ser Leu Gly Lys Ser Ser Arg Gly Leu Lys Ile Tyr Ala
            580                 585                 590

Met Glu Ile Ser Asp Asn Pro Gly Asp His Glu Leu Gly Glu Pro Glu
        595                 600                 605

Phe Arg Tyr Thr Ala Gly Ile His Gly Asn Glu Val Leu Gly Arg Glu
    610                 615                 620

Leu Leu Leu Leu Leu Met Gln Tyr Leu Cys Gln Glu Tyr Arg Asp Gly
625                 630                 635                 640

Asn Pro Arg Val Arg Asn Leu Val Gln Asp Thr Arg Ile His Leu Val
                645                 650                 655
```

-continued

```
Pro Ser Leu Asn Pro Asp Gly Tyr Glu Val Ala Ala Gln Met Gly Ser
            660                 665                 670

Glu Phe Gly Asn Trp Ala Leu Gly Leu Trp Thr Glu Glu Gly Phe Asp
        675                 680                 685

Ile Phe Glu Asp Phe Pro Asp Leu Asn Ser Val Leu Trp Ala Ala Glu
    690                 695                 700

Glu Lys Lys Trp Val Pro Tyr Arg Val Pro Asn Asn Leu Pro Ile
705                 710                 715                 720

Pro Glu Arg Tyr Leu Ser Pro Asp Ala Thr Val Ser Thr Glu Val Arg
                725                 730                 735

Ala Ile Ile Ser Trp Met Glu Lys Asn Pro Phe Val Leu Gly Ala Asn
            740                 745                 750

Leu Asn Gly Gly Glu Arg Leu Val Ser Tyr Pro Tyr Asp Met Ala Arg
        755                 760                 765

Thr Pro Ser Gln Glu Gln Leu Leu Ala Glu Ala Leu Ala Ala Ala Arg
    770                 775                 780

Gly Glu Asp Asp Gly Val Ser Glu Ala Gln Glu Thr Pro Asp His
785                 790                 795                 800

Ala Ile Phe Arg Trp Leu Ala Ile Ser Phe Ala Ser Ala His Leu Thr
                805                 810                 815

Met Thr Glu Pro Tyr Arg Gly Gly Cys Gln Ala Gln Asp Tyr Thr Ser
            820                 825                 830

Gly Met Gly Ile Val Asn Gly Ala Lys Trp Asn Pro Arg Ser Gly Thr
        835                 840                 845

Phe Asn Asp Phe Ser Tyr Leu His Thr Asn Cys Leu Glu Leu Ser Val
    850                 855                 860

Tyr Leu Gly Cys Asp Lys Phe Pro His Glu Ser Glu Leu Pro Arg Glu
865                 870                 875                 880

Trp Glu Asn Asn Lys Glu Ala Leu Leu Thr Phe Met Glu Gln Val His
                885                 890                 895

Arg Gly Ile Lys Gly Val Val Thr Asp Glu Gln Gly Ile Pro Ile Ala
            900                 905                 910

Asn Ala Thr Ile Ser Val Ser Gly Ile Asn His Gly Val Lys Thr Ala
        915                 920                 925

Ser Gly Gly Asp Tyr Trp Arg Ile Leu Asn Pro Gly Glu Tyr Arg Val
930                 935                 940

Thr Ala His Ala Glu Gly Tyr Thr Ser Ser Ala Lys Ile Cys Asn Val
945                 950                 955                 960

Asp Tyr Asp Ile Gly Ala Thr Gln Cys Asn Phe Ile Leu Ala Arg Ser
                965                 970                 975

Asn Trp Lys Arg Ile Arg Glu Ile Leu Ala Met Asn Gly Asn Arg Pro
            980                 985                 990

Ile Leu Gly Val Asp Pro Ser Arg Pro Met Thr Pro Gln Arg Arg
        995                 1000                1005

Met Gln Gln Arg Arg Leu Gln Tyr Arg Leu Arg Met Arg Glu Gln Met
    1010                1015                1020

Arg Leu Arg Arg Leu Asn Ser Thr Ala Gly Pro Ala Thr Ser Pro Thr
1025                1030                1035                1040

Pro Ala Leu Met Pro Pro Pro Ser Pro Thr Pro Ala Ile Thr Leu Arg
                1045                1050                1055

Pro Trp Glu Val Leu Pro Thr Thr Thr Ala Gly Trp Glu Glu Ser Glu
            1060                1065                1070
```

```
Thr Glu Thr Tyr Thr Glu Val Val Thr Glu Phe Glu Thr Tyr Gly
        1075                1080                1085

Thr Asp Leu Glu Val Glu Glu Ile Glu Glu Glu Glu Glu Glu Glu
        1090                1095                1100

Glu Glu Met Asp Thr Gly Leu Thr Phe Pro Leu Thr Thr Val Glu Thr
1105                1110                1115                1120

Tyr Thr Val Asn Phe Gly Asp Phe
                1125

<210> SEQ ID NO 31
<211> LENGTH: 764
<212> TYPE: PRT
<213> ORGANISM: Mus musculus

<400> SEQUENCE: 31

Met Ala Arg Leu Gly Thr Ala Cys Pro Ala Leu Ala Leu Ala
  1               5                  10                  15

Leu Val Ala Val Ala Leu Ala Gly Val Arg Ala Gln Gly Ala Ala Phe
                 20                  25                  30

Glu Glu Pro Asp Tyr Tyr Ser Gln Glu Leu Trp Arg Arg Gly Arg Tyr
             35                  40                  45

Tyr Gly His Pro Glu Pro Glu Pro Glu Pro Glu Leu Phe Ser Pro Ser
     50                  55                  60

Met His Glu Asp Leu Arg Val Glu Glu Gln Glu Gln Gln Glu Pro His
 65                  70                  75                  80

Gln Gln Gly His Arg Thr Pro Lys Lys Ala Ile Lys Pro Lys Lys Ala
                 85                  90                  95

Pro Lys Arg Glu Lys Leu Val Ala Glu Thr Pro Pro Gly Lys Asn
            100                 105                 110

Ser Asn Arg Lys Gly Arg Arg Ser Lys Asn Leu Glu Lys Ala Ala Ser
            115                 120                 125

Asp Asp His Gly Val Pro Val Ala His Glu Asp Val Arg Glu Ser Cys
130                 135                 140

Pro Pro Leu Gly Leu Glu Thr Leu Lys Ile Thr Asp Phe Gln Leu His
145                 150                 155                 160

Ala Ser Thr Ser Lys Arg Tyr Gly Leu Gly Ala His Arg Gly Arg Leu
                165                 170                 175

Asn Ile Gln Ala Gly Ile Asn Glu Asn Asp Phe Tyr Asp Gly Ala Trp
            180                 185                 190

Cys Ala Gly Arg Asn Asp Leu His Gln Trp Ile Glu Val Asp Ala Arg
        195                 200                 205

Arg Leu Thr Lys Phe Thr Gly Val Ile Thr Gln Gly Arg Asn Ser Leu
    210                 215                 220

Trp Leu Ser Asp Trp Val Thr Ser Tyr Lys Val Met Val Ser Asn Asp
225                 230                 235                 240

Ser His Thr Trp Val Thr Val Lys Asn Gly Ser Gly Asp Met Ile Phe
                245                 250                 255

Glu Gly Asn Ser Glu Lys Glu Ile Pro Val Leu Asn Glu Leu Pro Val
            260                 265                 270

Pro Met Val Ala Arg Tyr Ile Arg Ile Asn Pro Gln Ser Trp Phe Asp
        275                 280                 285

Asn Gly Ser Ile Cys Met Arg Met Glu Ile Leu Gly Cys Pro Leu Pro
    290                 295                 300

Asp Pro Asn Asn Tyr Tyr His Arg Arg Asn Glu Met Thr Thr Thr Asp
305                 310                 315                 320
```

-continued

```
Asp Leu Asp Phe Lys His His Asn Tyr Lys Glu Met Arg Gln Leu Met
                325                 330                 335
Lys Val Val Asn Glu Met Cys Pro Asn Ile Thr Arg Ile Tyr Asn Ile
            340                 345                 350
Gly Lys Ser His Gln Gly Leu Lys Leu Tyr Ala Val Glu Ile Ser Asp
            355                 360                 365
His Pro Gly Glu His Glu Val Gly Glu Pro Glu Phe His Tyr Ile Ala
        370                 375                 380
Gly Ala His Gly Asn Glu Val Leu Gly Arg Glu Leu Leu Leu Leu
385                 390                 395                 400
Leu His Phe Leu Cys Gln Glu Tyr Ser Ala Gln Asn Ala Arg Ile Val
                405                 410                 415
Arg Leu Val Glu Glu Thr Arg Ile His Ile Leu Pro Ser Leu Asn Pro
            420                 425                 430
Asp Gly Tyr Glu Lys Ala Tyr Glu Gly Gly Ser Glu Leu Gly Gly Trp
            435                 440                 445
Ser Leu Gly Arg Trp Thr His Asp Gly Ile Asp Ile Asn Asn Asn Phe
            450                 455                 460
Pro Asp Leu Asn Ser Leu Leu Trp Glu Ala Glu Asp Gln Gln Asn Ala
465                 470                 475                 480
Pro Arg Lys Val Pro Asn His Tyr Ile Ala Ile Pro Glu Trp Phe Leu
                485                 490                 495
Ser Glu Asn Ala Thr Val Ala Thr Glu Thr Arg Ala Val Ile Ala Trp
            500                 505                 510
Met Glu Lys Ile Pro Phe Val Leu Gly Gly Asn Leu Gln Gly Gly Glu
            515                 520                 525
Leu Val Val Ala Tyr Pro Tyr Asp Met Val Arg Ser Leu Trp Lys Thr
            530                 535                 540
Gln Glu His Thr Pro Thr Pro Asp Asp His Val Phe Arg Trp Leu Ala
545                 550                 555                 560
Tyr Ser Tyr Ala Ser Thr His Arg Leu Met Thr Asp Ala Arg Arg Arg
                565                 570                 575
Val Cys His Thr Glu Asp Phe Gln Lys Glu Glu Gly Thr Val Asn Gly
            580                 585                 590
Ala Ser Trp His Thr Val Ala Gly Ser Leu Asn Asp Phe Ser Tyr Leu
            595                 600                 605
His Thr Asn Cys Phe Glu Leu Ser Ile Tyr Val Gly Cys Asp Lys Tyr
        610                 615                 620
Pro His Glu Ser Glu Leu Pro Glu Glu Trp Glu Asn Asn Arg Glu Ser
625                 630                 635                 640
Leu Ile Val Phe Met Glu Gln Val His Arg Gly Ile Lys Gly Ile Val
                645                 650                 655
Arg Asp Leu Gln Gly Lys Gly Ile Ser Asn Ala Val Ile Ser Val Glu
            660                 665                 670
Gly Val Asn His Asp Ile Arg Thr Ala Ser Asp Gly Asp Tyr Trp Arg
            675                 680                 685
Leu Leu Asn Pro Gly Glu Tyr Val Val Thr Ala Lys Ala Glu Gly Phe
            690                 695                 700
Ile Thr Ser Thr Lys Asn Cys Met Val Gly Tyr Asp Met Gly Ala Thr
705                 710                 715                 720
Arg Cys Asp Phe Thr Leu Thr Lys Thr Asn Leu Ala Arg Ile Arg Glu
                725                 730                 735
```

-continued

```
Ile Met Glu Thr Phe Gly Lys Gln Pro Val Ser Leu Pro Ser Arg Arg
            740                 745                 750

Leu Lys Leu Arg Gly Arg Lys Arg Gln Arg Gly
        755                 760
```

<210> SEQ ID NO 32
<211> LENGTH: 722
<212> TYPE: PRT
<213> ORGANISM: Mus musculus

<400> SEQUENCE: 32

```
Met Trp Gly Leu Leu Ala Val Thr Ala Phe Ala Pro Ser Val Gly
 1               5                  10                  15

Leu Gly Leu Gly Ala Pro Ser Ala Ser Val Pro Gly Leu Ala Pro Gly
                20                  25                  30

Ser Thr Leu Ala Pro His Ser Val Ala Gln Pro Ser Thr Lys Ala
            35                  40                  45

Asn Glu Thr Ser Glu Arg His Val Arg Leu Arg Val Ile Lys Lys Lys
 50                  55                  60

Lys Ile Val Val Lys Lys Arg Lys Lys Leu Arg His Pro Gly Pro Leu
 65                  70                  75                  80

Gly Thr Ala Arg Pro Val Val Pro Thr His Pro Ala Lys Thr Leu Thr
                85                  90                  95

Leu Pro Glu Lys Gln Glu Pro Gly Cys Pro Pro Leu Gly Leu Glu Ser
            100                 105                 110

Leu Arg Val Ser Asp Ser Gln Leu Glu Ala Ser Ser Ser Gln Ser Phe
            115                 120                 125

Gly Leu Gly Ala His Arg Gly Arg Leu Asn Ile Gln Ser Gly Leu Glu
        130                 135                 140

Asp Gly Asp Leu Tyr Asp Gly Ala Trp Cys Ala Glu Gln Gln Asp Thr
145                 150                 155                 160

Glu Pro Trp Leu Gln Val Asp Ala Lys Asn Pro Val Arg Phe Ala Gly
                165                 170                 175

Ile Val Thr Gln Gly Arg Asn Ser Val Trp Arg Tyr Asp Trp Val Thr
            180                 185                 190

Ser Phe Lys Val Gln Phe Ser Asn Asp Ser Gln Thr Trp Trp Lys Ser
        195                 200                 205

Arg Asn Ser Thr Gly Met Asp Ile Val Phe Pro Ala Asn Ser Asp Ala
210                 215                 220

Glu Thr Pro Val Leu Asn Leu Pro Glu Pro Gln Val Ala Arg Phe
225                 230                 235                 240

Ile Arg Leu Leu Pro Gln Thr Trp Phe Gln Gly Gly Val Pro Cys Leu
                245                 250                 255

Arg Ala Glu Ile Leu Ala Cys Pro Val Ser Asp Pro Asn Asp Leu Phe
            260                 265                 270

Pro Glu Ala His Thr Leu Gly Ser Ser Asn Ser Leu Asp Phe Arg His
        275                 280                 285

His Asn Tyr Lys Ala Met Arg Lys Leu Met Lys Gln Val Asn Glu Gln
        290                 295                 300

Cys Pro Asn Ile Thr Arg Ile Tyr Ser Ile Gly Lys Ser His Gln Gly
305                 310                 315                 320

Leu Lys Leu Tyr Val Met Glu Met Ser Asp His Pro Gly Glu His Glu
                325                 330                 335

Leu Gly Glu Pro Glu Val Arg Tyr Val Ala Gly Met His Gly Asn Glu
            340                 345                 350
```

-continued

```
Ala Leu Gly Arg Glu Leu Leu Leu Leu Met Gln Phe Leu Cys His
            355                 360                 365
Glu Phe Leu Arg Gly Asp Pro Arg Val Thr Arg Leu Leu Thr Glu Thr
    370                 375                 380
Arg Ile His Leu Leu Pro Ser Met Asn Pro Asp Gly Tyr Glu Thr Ala
385                 390                 395                 400
Tyr His Arg Gly Ser Glu Leu Val Gly Trp Ala Glu Gly Arg Trp Thr
                405                 410                 415
His Gln Gly Ile Asp Leu Asn His Asn Phe Ala Asp Leu Asn Thr Gln
            420                 425                 430
Leu Trp Tyr Ala Glu Asp Asp Gly Leu Val Pro Asp Thr Val Pro Asn
            435                 440                 445
His His Leu Pro Leu Pro Thr Tyr Tyr Thr Leu Pro Asn Ala Thr Val
            450                 455                 460
Ala Pro Glu Thr Trp Ala Val Ile Lys Trp Met Lys Arg Ile Pro Phe
465                 470                 475                 480
Val Leu Ser Ala Asn Leu His Gly Gly Glu Leu Val Val Ser Tyr Pro
                485                 490                 495
Phe Asp Met Thr Arg Thr Pro Trp Ala Ala Arg Glu Leu Thr Pro Thr
                500                 505                 510
Pro Asp Asp Ala Val Phe Arg Trp Leu Ser Thr Val Tyr Ala Gly Thr
            515                 520                 525
Asn Arg Ala Met Gln Asp Thr Asp Arg Arg Pro Cys His Ser Gln Asp
            530                 535                 540
Phe Ser Leu His Gly Asn Val Ile Asn Gly Ala Asp Trp His Thr Val
545                 550                 555                 560
Pro Gly Ser Met Asn Asp Phe Ser Tyr Leu His Thr Asn Cys Phe Glu
                565                 570                 575
Val Thr Val Glu Leu Ser Cys Asp Lys Phe Pro His Glu Lys Glu Leu
                580                 585                 590
Pro Gln Glu Trp Glu Asn Asn Lys Asp Ala Leu Leu Thr Tyr Leu Glu
            595                 600                 605
Gln Val Arg Met Gly Ile Thr Gly Val Val Arg Asp Lys Asp Thr Glu
            610                 615                 620
Leu Gly Ile Ala Asp Ala Val Ile Ala Val Glu Gly Ile Asn His Asp
625                 630                 635                 640
Val Thr Thr Ala Trp Gly Gly Asp Tyr Trp Arg Leu Leu Thr Pro Gly
                645                 650                 655
Asp Tyr Val Val Thr Ala Ser Ala Glu Gly Tyr His Thr Val Arg Gln
                660                 665                 670
His Cys Gln Val Thr Phe Glu Glu Gly Pro Val Pro Cys Asn Phe Leu
            675                 680                 685
Leu Thr Lys Thr Pro Lys Glu Arg Leu Arg Glu Leu Leu Ala Thr Arg
            690                 695                 700
Gly Lys Leu Pro Pro Asp Leu Arg Lys Leu Glu Arg Leu Arg Gly
705                 710                 715                 720
Gln Lys
```

AORTIC CARBOXYPEPTIDASE-LIKE PROTEIN AND NUCLEIC ACIDS ENCODING SAME

RELATED APPLICATIONS

This application claims priority to U.S. Ser. No. 60/159,613 filed Oct. 14, 1999, U.S. Ser. No. 60/175,534, filed Jan. 11, 2000 and U.S. Ser. No. 60/224,086, filed Aug. 9, 2000. The contents of these applications are incorporated herein by reference in their entireties.

FIELD OF THE INVENTION

The invention relates in general to polynucleotides and polypeptides encoded thereby. The invention relates more particularly to nucleotides encoding polypeptides related to human aortic carboxypeptidase.

BACKGROUND OF THE INVENTION

The carboxypeptidases are a family of hydrolase enzymes that remove the amino acid at the free carboxyl (C) end of a polypeptide chain. Members of the carboxypeptidase family have been implicated in multiple biological activities.

Carboxypeptidases can be divided into at least two subfamilies of metallocarboxypeptidases. One subfamily includes the pancreatic carboxypeptidase-like subfamily. Its members include, e.g., carboxypeptidase A, carboxypetpidase A2, carboxypeptidase B, and carboxypeptidase B2.

A second subfamily includes regulatory B-type carboxypeptidases. Its members include, e.g., carboxypeptidase H, carboxypeptidease M, carboxypeptidase N, carboxypeptidase Z, AEBP1, ACPLX, Ms CPX1, and MsCPX2. Members of this subfamily have been implicated in activities that include regulation of polypeptide hormone processing activity and processing of extracellular peptides with carboxy-terminal arginine residues. In addition, carboxypeptidases present at the surface of vascular smooth muscle cells, such as aortic smooth muscle cells, have been reported to exert a complex influence on the level of biologically active vasoactive peptides, e.g. bradykinin, angiotensin II, which influence the tone and caliber of blood vessels. Carboxypeptidases have also been reported to be are responsible for a catabolic inactivation of vasoactive peptides.

SUMMARY OF THE INVENTION

The present invention is based upon the discovery of a novel human nucleic acid sequence encoding a polypeptide having sequence similarity to previously described members of the carboxypeptidase. The aortic carboxypeptidase-like nucleic acids, polynucleotides, proteins and polypeptides, or fragments thereof described herein are collectively referred to as ACPLX nucleic acids and polypeptides. ACPLX nucleic acids include those found in SEQ ID NO: 1, and the polypeptide encoded by SEQ ID NO:2.

Accordingly, one aspect of the present invention includes an isolated aortic carboxypeptidase-like nucleic acid molecule that includes a nucleotide sequence encoding a polypeptide that includes the amino acid sequence of SEQ ID NO:2. In various embodiments, the nucleic acid molecule can include a nucleotide sequence that includes SEQ ID NO:1. Alternatively, the encoded aortic carboxypeptidase-like protein (ACPLX) may possess a variant amino acid sequence, thereby having an identity or similarity less than 100% to the disclosed amino acid sequences.

The invention further includes an isolated polypeptide that includes the amino acid sequence of SEQ ID NO:2. Also included is a variant of a mature form of the amino acid sequence, or a variant of the amino acid, given by SEQ ID NO:2. In various embodiments, no more than 15%, 10%, 9%, 8%, 5%, 3%, 2%, or 1% of the amino acid residues in the sequence are changed to a different amino acid.

The invention yet further includes an antibody that immunospecifically binds to ACPLX. In the preferred embodiment, the antibody is monoclonal and of human origin. Such antibodies are most useful in treating a pathological condition in a subject wherein the treatment includes administering the antibody to the subject.

Also included in the invention is a method of producing an ACPLX by culturing a host cell expressing the aortic carboxypeptidase-like nucleic acids, described herein, under conditions in which the nucleic acid molecule is expressed.

The invention yet further includes a method of detecting the presence of an aortic carboxypeptidase-like polypeptide in a sample from a mammal, e.g., a human, by introducing a sample from the mammal with an antibody that immunospecifically binds to one of the polypeptides, and then detecting the formation of reaction complexes including the antibody and the polypeptide in the sample. Detecting the formation of complexes in the sample indicates the presence of the polypeptide in the sample.

Also included in the invention is a method of detecting the presence of an aortic carboxypeptidase-like nucleic acid molecule in a sample from a mammal, e.g. a human, by introducing the sample with a nucleic acid probe that selectively binds to the nucleic acid, and then determining whether the nucleic acid binds to a nucleic acid molecule in the sample. Binding of the nucleic acid probe indicates the nucleic acid molecule is present in the sample.

The invention yet still further includes a method of identifying a potential therapeutic agent for use in the treatment of a pathology associated with altered levels of an aortic carboxypeptidase-like nucleic acid sample from a mammal e.g., a human. The method includes introducing a cell expressing the polypeptide with a composition that is a candidate substance for a therapeutic agent. Where the property or function of the candidate substance is altered in the presence of the cell, the substance is identified as a potential therapeutic agent.

The invention also includes a method of treating or preventing a pathological condition in a mammal e.g., a human, associated with the polypeptide described herein, by administering to the subject an ACPLX in an amount sufficient to alleviate the pathological condition. Alternatively, the mammal may be treated by administering an antibody, as described herein, in an amount sufficient to alleviate the pathological condition.

Pathological states for which methods of treatment of the invention are envisioned include a cancer e.g., breast and ovarian, hypertensive disorder, vascular endothelial disorders e.g. atherosclerosis, processing and/or transport of the vasopressin-ncurophysin pre-hormone product.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 1 is a representation of a nucleotide sequence (SEQ ID NO:1) that encodes an ACPLX polypeptide of the invention.

FIG. 2 is a representation of an ACPLX polypeptide sequence (SEQ ID NO:2) encoded by the nucleotide sequence shown in FIG. 1.

FIGS. 3A and 3B are a comparison of the amino acid sequences of a mouse AEBP1 polypeptide (SEQ ID NO:28) ("Q61281"), a human AEBP1 polypeptide (SEQ ID NO:29) ("Q14113"), a mouse aortic carboxypeptidase-like 2 polypeptide (SEQ ID NO:30) ("O88442"), a mouse carboxypeptidase X2 polypeptide (SEQ ID NO:31) ("O54860"), and an ACPLX polypeptide of the invention (SEQ ID NO:2) ("ALO35460_GENESCAN_predicted_pep").

FIG. 4 is a comparison showing regions of identity and of conserved amino acid substitutions in the amino acid sequences of a mouse CPPX1 polypeptide (AFO77738) and an ACPLX polypeptide (SEQ ID NO:2) ("ALO35460_GENESCAN_predicted_pep").

FIGS. 6A–6C are histograms representing relative expression of an ACPLX nucleic acid in various cell types and tissues.

FIGS. 7A–7C are histograms representing relative expression of an ACPLX nucleic acid of the invention in various tissues using a probe set AG86b.

DETAILED DESCRIPTION OF THE INVENTION

Figure 5:
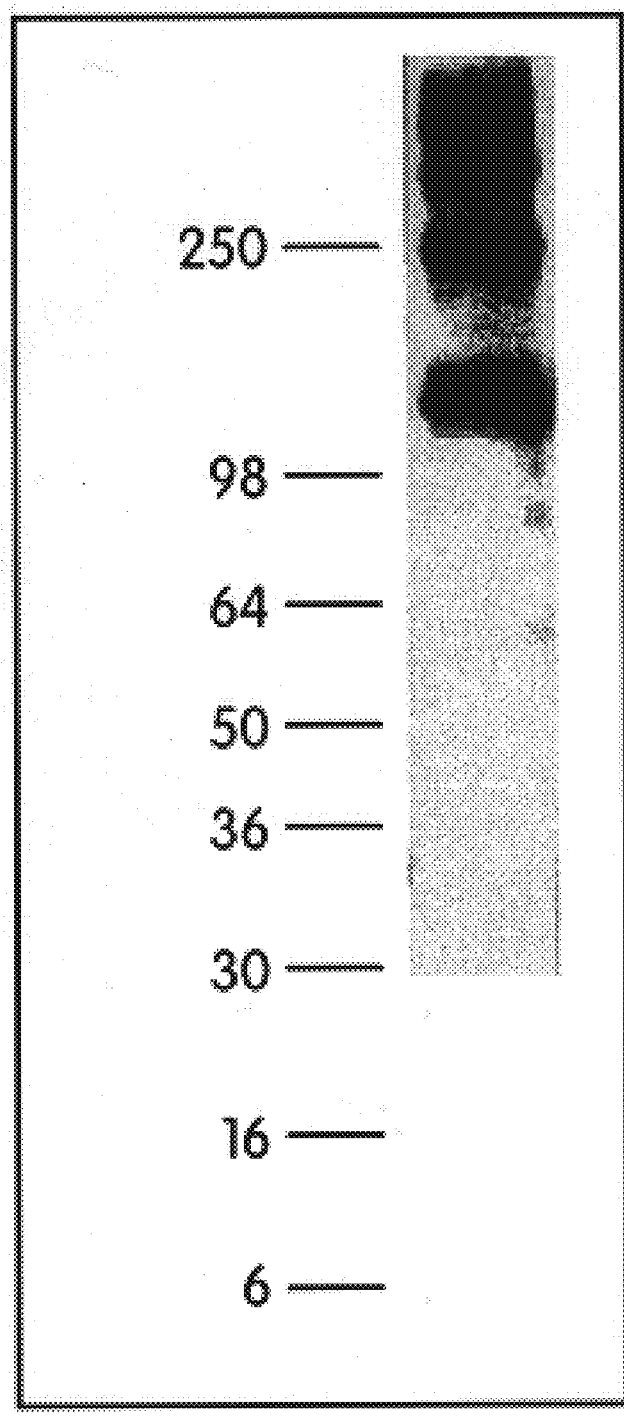
FIG. 5 is a representation of a western blot showing expression of an ACPLX polypeptide by 293 cells.

The invention provides nucleic acids encoding a novel member of the aortic carboxypeptidase like protein family. Nucleic acids and polypeptides related to the novel aortic carboxypetpidase are referred to generally herein as ACPLX nucleic acids and polypeptides. Included in the invention is a nucleic acid of 2382 nucleotides in length (SEQ ID NO:1). The sequence shown in FIG. 1 and is also referred to herein as AL035460A.

An open reading frame ("ORF") of 2,205 nucleotides from 101 to 2305 is present in the nucleic acid sequence shown in FIG. 1. The ORF begins with an atg initiation codon at nucleotide 101 and ends with a tga codon beginning at nucleotide 2305. A putative untranslated region upstream from the initiation codon is underlined in FIG. 1. The start and stop codons are in bold letters. The ORF encodes a polypeptide of 734 amino acid residues (SEQ ID NO:2). The sequence of the encoded polypeptide is presented in FIG. 2.

The disclosed ACPLX nucleic acid sequence is identical at 1760 of 2129 bases (82% identity) to a 2379 bp Mus musculus metallocarboxypeptidase CPX-1 mRNA (GENBANK-ID: AF077738). The homology is present between bases 73 and 2201 of the sequence of AL035460A and bases 112 and 2236 of the sequence of AF077738.

The encoded amino acid sequence is also related to murine metallocarboxypeptidase CPX-1 (SPTREMBL-ACC:Q9Z100), which is a polypeptide of 722 residues. 622 of 733 residues (84%) of the encoded ACPLX polypeptide are identical to, and 661 of 733 residues (90%) positive with, the murine metallocarboxypeptidase CPX-1 polypeptide. The disclosed ACPLX polypeptide sequence includes additional residues not found in ACC:Q9Z100. The disclosed ACPLX polypeptide also includes sequence s related to the 764 residue murine carboxypeptidase X2 (SPTREMBL-ACC:O54860). For the regions 41–733 of the disclosed ACPLX polypeptide and residues 61–759 of murine carboxypeptidase X2, 377 of 698 residues (54%) are identical to, and 486 of 698 residues (69%) are positive.

Figure 3:
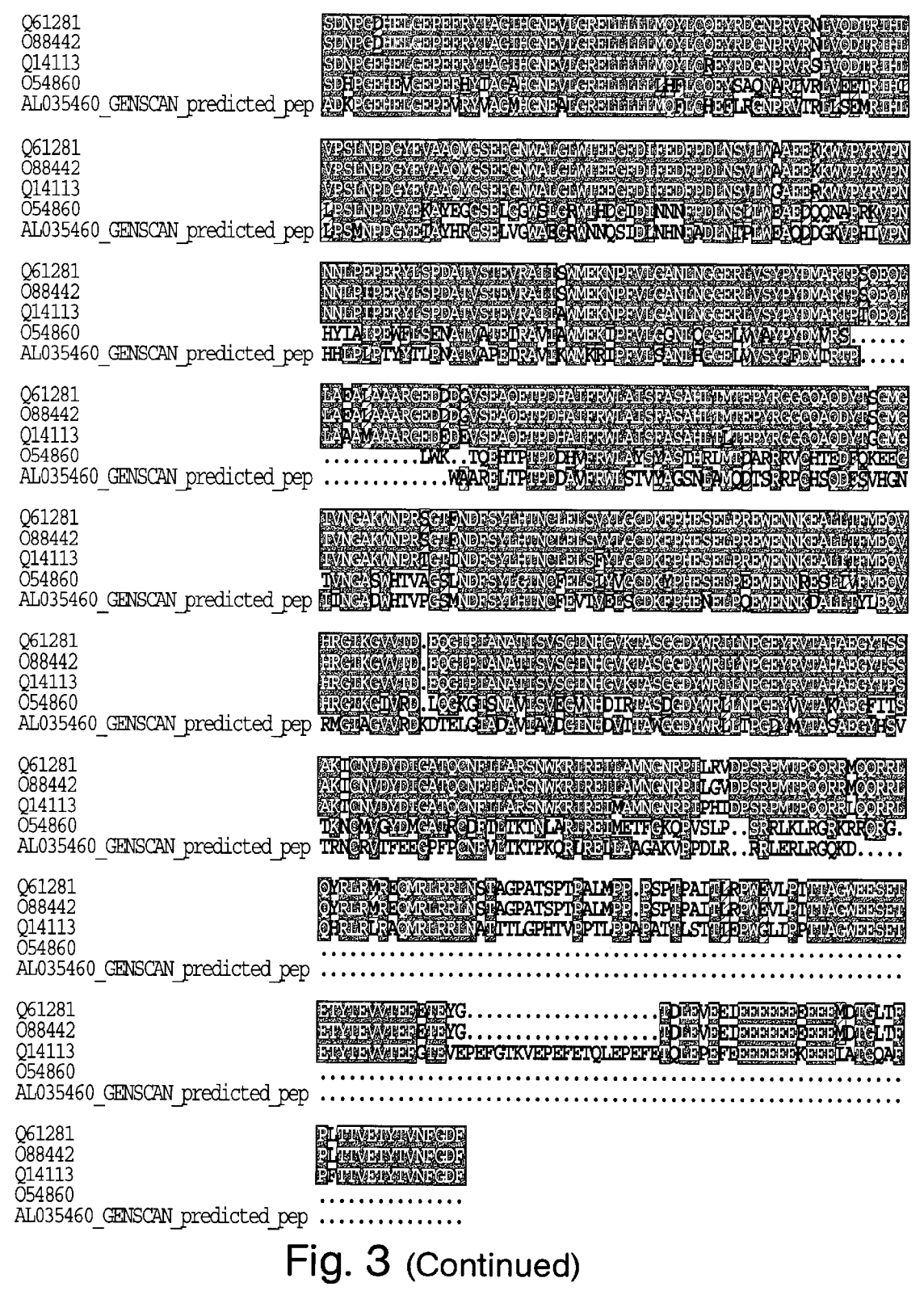

A multiple sequence alignment between the disclosed ACPLX polypeptide and other carboxypeptidase family members is presented in FIGS. 3A and 3B. Shown is a comparison of the amino acid sequences of a mouse AEBP1 polypeptide (SEQ ID NO:28) ("Q61281"), a human AEBP1 polypeptide (SEQ ID NO:29) ("Q14113"), a mouse aortic carboxypeptidase-like 2 polypeptide (SEQ ID NO:30) ("O88442"), a mouse carboxypeptidase X2 polypeptide (SEQ ID NO:31) ("O54860"), and an ACPLX polypeptide of the invention (SEQ ID NO:2) ("ALO35460_GENESCAN_predicted_pep"). The disclosed ACPLX polypeptide is identical at 202 of 366 residues (55%) to, and positive at 260 of 366 residues (71%) with, the Q61281 protein. The Q61281 protein is described in He et al., Nature 378:92–96, 1995.

The disclosed ACPLX polypeptide is identical at 224 of 408 residues (54%) to, and positive at 286 of 408 residues (70%) with, the Q14113 protein. The Q14113 protein is discussed in Ohno et al., Biochem Biophys. Res. Comm. 228:411–14, 1996.

The disclosed ACPLX polypeptide is identical at 334 of 623 residues (53%) to, and is positive at 433 of 623 residues (69%) with, the O88442 protein. The O88442 protein is described in Layne et al., J. Biol. Chem. 273:15654–60, 1998.

The disclosed ACPLX polypeptide is identical at 377 of 698 residues to (54%) and is positive at 486 of 698 residues (69%) with, the O54860 protein.

Figure 4:
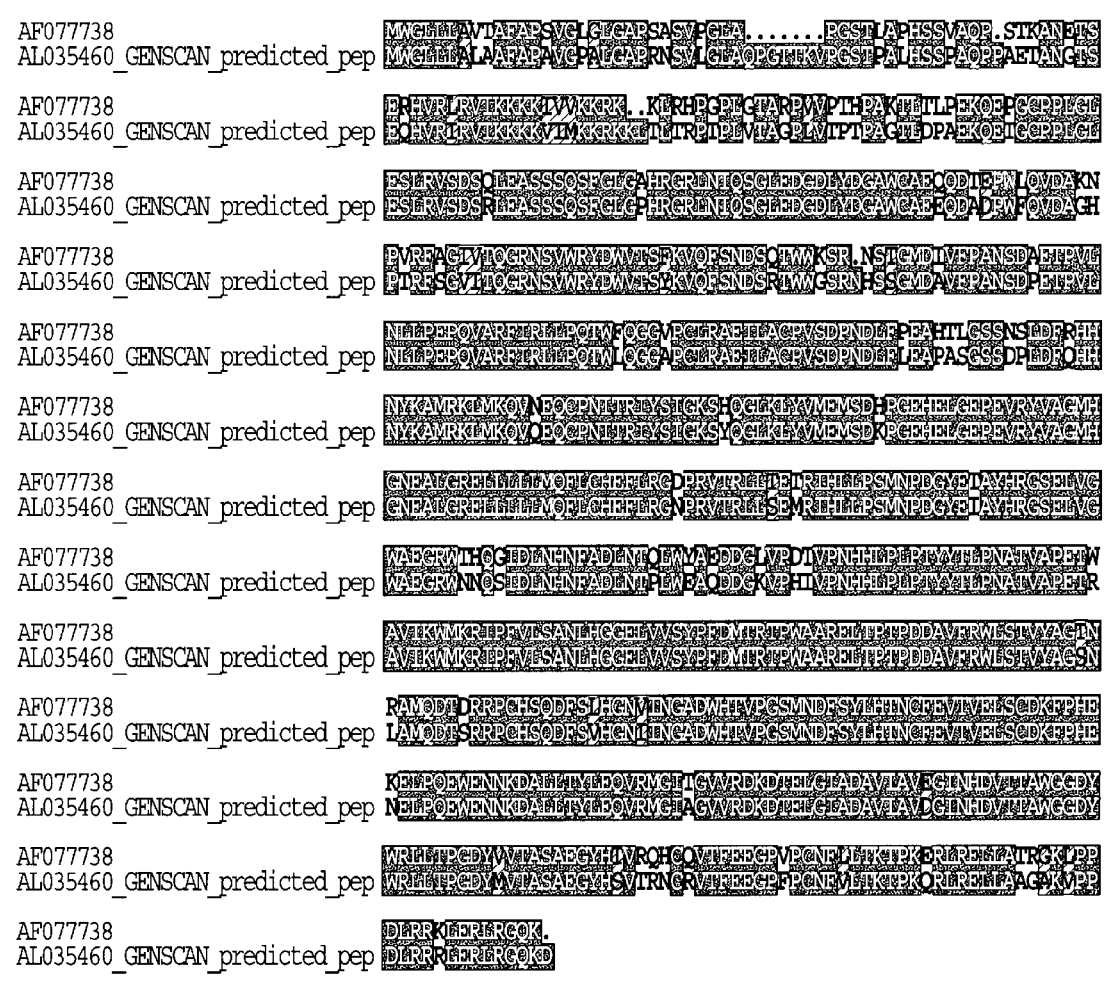

FIG. 4 shows that the disclosed ACPLX polypeptide is also highly similar to murine CPX-1. Shown is a comparison showing regions of identity and of conserved amino acid substitutions in the amino acid sequences of a mouse CPPX1 polypeptide (AFO77738) and an ACPLX polypeptide (SEQ ID NO:2) ("ALO35460_GENESCAN_predicted_pep").

The disclosed ACPLX polypeptide sequence includes multiple domains. These domains are shown in FIG. 2. These include an amino-terminal signal peptide-like sequence, a 161-residue discoidin domain and two carboxypeptidase (CP) catalytic cleavage domains with zinc binding residues. The first CP domain is at residues 299–409, and the second CP domain extends over residues 421–689. Also present in the disclosed ACPLX polypeptide is a calcium-binding site that is highly conserved among the metallocarboxypeptidase family members.

The sequence homologies demonstrate that ACPLX is a member of the regulatory B-type carboxypeptidase subfamily and can be considered, e.g., a human ortholog to murine CPX-1. The relationship between the new polypeptide and other regulatory B-type carboxypeptidases is presented in Table I.

Table I. The Two Metallocarboxypeptidase Subfamilies.

Pancreatic carboxypeptidase-like subfamily.

| | |
|---|---|
| Carboxypeptidase A | Pancreatic-digestive |
| Carboxypeptidase A2 | Pancreatic procarboxypeptidase acts on aromatic C-terminal residues. |

-continued

| | |
|---|---|
| Carboxypeptidase B | Pancreatic-digestive |
| Carboxypeptidase B2 | (U) Thrombin-activatable fibrinolysis inhibitor (TAFI) (plasminogen activator) |

The regulatory B-type carboxypeptidase subfamily.

| | |
|---|---|
| Carboxypeptidase E | (CBPE) Processes prohormone intermediates such as proinsulin (Fricker, et al., Trends Biochem Sci. 24:390–93, 1999). |
| Carboxypeptidase M | Regulates peptide hormone activity (Rehli et al., J Biol Chem. 270:15644–49, 1995). |
| Carboxypeptidase D | A homolog of duck gp180, a 180 kDa hepatitis B virus-binding protein (McGwire et al., Life Sci. 60:715–24, 1997). |
| Carboxypeptidase N | Cleaves and inactivates kininase-1 and anaphyla-toxin in the serum (Tan et. al., Anesthesiology 70:267–75, 1989). |
| Carboxypeptidase Z | May process extracellular peptides or proteins with C-terminal Arg residues (Song et al., J Biol Chem. 272:10543–50, 1997). |
| AEBP1 | Regulates transcription by cleavage of factors involved in transcription (Muise, et al., Biochem J. 343:341–45, 1999). |
| ACPLX | Functioning of differentiated vascular smooth muscle cells (Layne, et al., J. Biol. Chem. 273:15654–60, 1998). |
| Ms_CPX2 | Possibly acts as a binding protein rather than as an active carboxypeptidase (Xin, et. al., DNA Cell Biol 17:897–909, 1998). |
| Ms_CPX1 | May have a role in development by mediating cell interactions via its discoidin domain (Lei , et al., DNA Cell Biol. 18:175–85, 1999). |

The CP domains have 95 and 91% amino acid identity, respectively (see Table II), with CPX-1, a mouse homolog that lacks several active-site residues that are important for catalytic activity (Lei , et al., DNA Cell Biol. 18:175–85, 1999). The catalytic sites that are absent in CPX-1 are also absent in the carboxypeptidase-like protein of the present invention, indicating that an ALCLPLX polypeptide according to the invention may lack enzymatic cleavage function. However, a zinc-binding region, absent in most human metallocarboxypeptidases, is present in both the protein of the present invention and CPX-1. The zinc-binding region is located within the second catalytic domain at H498 and H491, respectively, of the two polypeptides. The function of this extra zinc binding domain is unknown may serve as an additional enzymatic site on the molecule.

The extent of sequence homology between members of metallocarboxypeptidase family members and an ALCLPLX polypeptide of the invention is shown Table II.

TABLE 11

Protein domain sequence homology between members of the metallocarboxypeptidase family and the polypeptide encoded by AL035460_A.

| Gene ID | Total | Discoidin | Ca | 1st CP | 2nd CP | Zn |
|---|---|---|---|---|---|---|
| Hu_CBPA | | | | POOR | | |
| Ru_CBPA2 | | | | POOR | | |
| Hu_CBPB | | | | POOR | | |
| Hu_CBPB2 (U) | | | | POOR | | |
| Hu_CBPR (E) | 50% | 5% | 77% | 74% | 67% | Y |
| Hu_CBPM | POOR | 0% | 46% | 66% | 59% | Y |
| Hu_CBPD | POOR | 12% | 77% | 54% | 43% | Y |
| Hu_CBPN | POOR | 16% | 15% | 74% | 62% | N |
| Hu_CBPZ | POOR | 13% | 69% | 54% | 48% | Y |

TABLE 11-continued

Protein domain sequence homology between members of the metallocarboxypeptidase family and the polypeptide encoded by AL035460_A.

| Gene ID | Total | Discoidin | Ca | 1st CP | 2nd CP | Zn |
|---|---|---|---|---|---|---|
| Hu_AEBP1 | 53% | 52% | 92% | 71% | 54% | N |
| Ru_ACPLX(sgnl) | 53% | 51% | 92% | 71% | 54% | N |
| Ms_AEBP1 | 54% | 40% | 85% | 70% | 54% | N |
| Ms_ACPLX | 54% | 53% | 85% | 70% | 48% | N |
| Ms_CPX2 | 58% | 58% | 85% | 71% | 57% | N |
| Ms_CPX1 | 86% | 87% | 92% | 95% | 91% | Y |
| Ms_CBPH (E) | POOR | 5% | 77% | 74% | 65% | Y |

Ru = human
Ms = mouse
POOR = ≦50% match over full length
Total = % identity over the full-length protein sequences.
The remaining values are sorted as % homology within specific domains.
Ca = Calcium binding region.
1st CP = First carboxypeptidase catalytic domain (residues 299–409).
2nd CP = Second carboxypeptidase catalytic domain (residues 421–689).
Zen = Presence (Y) or absence (N) of the 3rd catalytic zinc binding site.

Based on a comparison of the first and second CP domains between the protein of the present invention and members of the human carboxypeptidase family, the disclosed ACPLX polypeptide (AL035460A protein) shares most sequence identity with carboxypeptidase E (hu_CBPH(E)). The percent identity for the first and second CP regions is 74 and 67%, respectively. CPE is a pro-hormone processing enzyme and is responsible for the production of insulin from its precursor pro-insulin. Mice expressing a mutant variant of CPH have improper insulin regulation with a resulting phenotype of obesity and hyperglycemia that can be suppressed by treatment with exogenous insulin (Naggert, et. al., Nature Genet. 10:135–142, 1995).

Although the disclosed ACPLX polypeptide shows some similarity to hu_CPF at the catalytic site, the disclosed ACPLX polypeptide differs greatly at the amino-terminus. For example, a discoidin domain is present in the disclosed ACPLX polypeptide, but is absent in hu_CPE. Discoidin domains on proteins allow the protein to interact with collagen on the surface of cells which mediates cell surface interactions between receptors and ligands (Vogel, FASEB J.13:S77–82,1999).

Therefore, the present carboxypeptidase-like protein may function as a binding protein that interacts with the cell surface mediating pro-hormone processing and/or interactions of hormones or other ligands with their receptors. The AL035460A carboxypeptidase nucleic acid is differentially down regulated in certain cancers such as breast cancer and ovarian cancer. An expression analysis of this sequence is provided in the Examples. The AL035460A nucleic acid or protein may therefore be used as a differential diagnostic agent in distinguishing normal from cancerous tissues, and as a therapeutic agent in the treatment of cancers such as these.

The novel nucleic acid of the invention encoding an aortic carboxypeptidase-like protein includes the protein whose sequence is provided in FIG. 1, or a fragment thereof. The invention also includes a mutant or variant nucleic acid any of whose bases may be changed from the corresponding base shown in FIG. 1, while still encoding a protein that maintains its aortic carboxypeptidase-like activities and physiological functions, or a fragment of such a nucleic acid. The invention further includes nucleic acids whose sequences are complementary to those just described. In the mutant or variant nucleic acid, up to 18% or more of the bases may be so changed.

The novel carboxypeptidase-like protein of the invention includes the protein whose sequence is provided in FIG. 2. The invention also includes a mutant or variant protein any of whose residues may be changed from the corresponding residue shown in FIG. 2 while still encoding a protein that maintains its aortic carboxypeptidase-like activities and physiological functions, or a functional fragment thereof. In the mutant or variant protein, up to 18% or more of the residues may be so changed. The invention further encompasses antibodies and antibody fragments, such as $F_{ab}$ or $(F_{ab})_2$, that bind immunospecifically to any of the proteins of the invention.

The nucleic acids and proteins of the carboxypeptidase-like proteins and encoding nucleic acids of the invention are useful in potential therapeutic applications implicated in various hypertensive disorders and/or vascular endothelial disorders. Additional therapeutic applications are related to a putative prohormone processing function attributed to the protein. For example, a cDNA encoding the aortic carboxypeptidase-like protein may be useful in gene therapy, and the aortic carboxypeptidase-like protein may be useful when administered to a subject in need thereof. By way of nonlimiting example, the compositions of the present invention have efficacy for treatment of patients suffering from hypertension, or atherosclerotic or comparable vascular pathologies. Additionally the compositions of the invention may be useful in treating conditions related to dysfunction in prohormone processing. The novel nucleic acid encoding aortic carboxypeptidase-like protein, and the protein of the invention, or fragments thereof, may further be useful in diagnostic applications, wherein the presence or amount of the nucleic acid or the protein are to be assessed. These materials are further useful in the generation of antibodies that bind immunospecifically to the novel substances of the invention for use in therapeutic or diagnostic methods.

The ALCLPX sequence present in AL035460A was derived from a genomic sequence obtained from chromosome 20 (20p12.3–13: GenBank Ace. AL035460). Gene mapping of AL035460 revealed the following diseases that map to the same location as the genomic sequence. It is therefore possible that the aortic carboxypeptidase-like gene product of AL035460A plays a role in one or more of the diseases Hallervorden-Spatz syndrome, Diabetes insipidus and/or tumor suppression in breast and ovarian cancer.

Hallervorden-Spatz syndrome (HSS) (OMIM #234200) is a rare, autosomal recessive neurodegenerative disorder with brain iron accumulation as a prominent finding. Clinical features include extrapyramidal dysfunction, onset in childhood, and a relentlessly progressive course. Histologic study reveals massive iron deposits in the basal ganglia. Systemic and cerebrospinal fluid iron levels are normal, as are plasma levels of ferritin, transferrin and ceruloplasmin. Conversely, in disorders of systemic iron overload, such as haemochromatosis, brain iron is not increased, which suggests that fundamental differences exist between brain and systemic iron metabolism and transport. In normal brain, non-haem iron accumulates regionally and is highest in basal ganglia. Pathologic brain iron accumulation is seen in common disorders, including Parkinson's disease, Alzheimer's disease and Huntington disease. In order to gain insight into normal and abnormal brain iron transport, metabolism and function, our approach was to map the gene for HSS. A primary genome scan was performed using samples from a large, consanguineous family (HS1). While this family was immensely powerful for mapping, the region demonstrating homozygosity in all affected members spans only 4 cM, requiring very close markers in order to detect linkage. The HSS gene maps to an interval flanked by D20S906 and D20S116 on chromosome 20p12.3–p13.1, inkage was confirmed in nine additional families of diverse ethnic backgrounds.

With relation to diabetes insipidus, arginine vasopressin and its corresponding neurophysin are synthesized in the form of a common precursor which is cleaved by proteolysis to yield the biologically functional peptides (Sachs et al., Recent Prog. Horm. Res. 25: 447–491, 1969). Rats with hereditary diabetes insipidus are deficient in synthesis of both arginine vasopressin and one species of neurophysin (Sunde ET al. Ann. N.Y. Acad. Sci. 248: 345–364, 1975).

Both of the peptide hormones arginine vasopressin and oxytocin (OXT) are synthesized in the supraoptic nucleus (SON) and paraventricular nucleus (PVN) of the hypothalamus together with their respective 'carrier' proteins, the neurophysins (Brownstein, M. J.; Russell, J. T.; Gainer, H. Synthesis, transport, and release of posterior pituitary hormones. *Science* 207: 373–378, 1980).

Vasopressin and oxytocin are produced by separate populations of magnocellular neurons in both nuclei. Together with the neurophysins they are packaged into neurosecretory vesicles and transported axonally to the nerve endings in the neurohypophysis, where they are either stored or secreted into the bloodstream. Vasopressin is synthesized as a much larger precursor which includes—besides the hormone—its carrier protein, neurophysin, and a glycoprotein. The functional domains of the protein precursor are coded by 3 exons separated by 2 introns. The first exon encodes the hormone, the second most of the carrier protein, and the third the glycoprotein. A single nucleotide deletion is found in the second exon in the Brattleboro rat with diabetes insipidus (Schmale et al., EMBO J. 3: 3289–93, 1984). In addition, a single amino acid mutation in the binding protein for vasopressin (neuphysin) was discovered in human subjects with autosomal dominant neurohypophyseal diabetes insipidus (Repaske et al., J Clin Endocrinol Metab 79(2):421–7, 1994).

As noted, diabetes insipidus may be caused by mutations in the vasopressin-neurophysin precursor protein, resulting in improper targeting of the hormone to secretory vesicles. As a result the precursor protein accumulates in the endoplasmic reticulum and never reaches the Golgi for further processing (Olias et al., DNA Cell Biol.15: 929–935, 1996). The gene product from AL035460A may be involved in the processing and/or transport of the vasopressin-neurophysin pre-hormone product. Defects in the function of the gene product from an ALCLPLX gene, e.g., AL035460A, may result in a defect in the production and secretion of active vasopressin, which may lead to the development of diabetes insipidus.

In relation to cancer, it is shown in the Examples that the AL035460A gene exhibits an expression profile consistent with it acting as a tumor suppressor gene in breast and ovarian cancer (i.e., reduced expression in tumor cell lines relative to normal tissue). Thus, such tumor cells are predicted to exhibit a decrease in growth rate both in vitro and in vivo following transfection and expression of an ACPLX nucleic acid, e.g., AL035460A.

ACPLX Nucleic Acids

The novel nucleic acids of the invention include those that encode an ACPLX polypeptide or protein. As used herein, the terms polypeptide and protein are interchangeable.

In some embodiments, an ALCPLX nucleic acid encodes a mature ACPLX polypeptide. As used herein, a "mature" form of a polypeptide or protein described herein relates to the product of a naturally occurring polypeptide or precursor form or proprotein. The naturally occurring polypeptide, precursor or proprotein includes, by way of nonlimiting example, the full length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps that may take place within the cell in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

Among the ALCLPLX nucleic acids is the nucleic acid whose sequence is provided in SEQ ID NO:1, or a fragment thereof. Additionally, the invention includes mutant or variant nucleic acids of SEQ ID NO:1, or a fragment thereof, any of whose bases may be changed from the corresponding base shown in SEQ ID ID NO:1, while still encoding a protein that maintains at least one of its ACPLX-like activities and physiological functions. The invention further includes the complement of the nucleic acid sequence of SEQ ID NO:1, including fragments, derivatives, analogs and homolog thereof. The invention additionally includes nucleic acids or nucleic acid fragments, or complements thereto, whose structures include chemical modifications.

One aspect of the invention pertains to isolated nucleic acid molecules that encode ACPLX proteins or biologically active portions thereof. Also included are nucleic acid fragments sufficient for use as hybridization probes to identify ACPLX-encoding nucleic acids (e.g., ACPLX mRNA) and fragments for use as polymerase chain reaction (PCR) primers for the amplification or mutation of ACPLX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated ACPLX nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO:1, or a complement of any of this nucleotide sequence, can be isolated using standard molecular biology techniques and the sequence information provided herein. Using all or a portion of the nucleic acid sequence of SEQ ID NO:1 as a hybridization probe, ACPLX nucleic acid sequences can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to ACPLX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO:1, or a complement thereof. Oligonucleotides may be chemically synthesized and may be used as probes.

In another embodiment, an isolated nucleic acid molecule of the invention includes a nucleic acid molecule that is a complement of the nucleotide sequence shown in SEQ ID NO:1. In another embodiment, an isolated nucleic acid molecule of the invention comprises a nucleic acid molecule that is a complement of the nucleotide sequence shown in SEQ ID ID NO:1, or a portion of this nucleotide sequence. A nucleic acid molecule that is complementary to the nucleotide sequence shown in SEQ ID NO: 1 is one that is sufficiently complementary to the nucleotide sequence shown in SEQ ID NO: 1 that it can hydrogen bond with little or no mismatches to the nucleotide sequence shown in SEQ ID NO:1, thereby forming a stable duplex. As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID ID NO:1, e.g., a fragment that can be used as a probe or primer, or a fragment encoding a biologically active portion of ACPLX. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g Ausubel, et al., CURRENT PROTOCOILS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appi. Math., 1981, 2: 482–489, which is incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of ACPLX polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for an ACPLX polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human ACPLX protein. Homologous nucleic acid sequences include those nucleic acid sequences that encode conservative amino acid substitutions (see below) in SEQ ID NO:2, as well as a polypeptide having ACPLX activity. Biological activities of the ACPLX proteins are described below. A homologous amino acid sequence does not encode the amino acid sequence of a human ACPLX polypeptide.

The nucleotide sequence determined from the cloning of the human ACPLX gene allows for the generation of probes and primers designed for use in identifying and/or cloning ACPLX homologues in other cell types, e.g., from other tissues, as well as ACPLX homologues from other mammals. The probe/primer typically comprises a substantially purified oligonucleotide. The oligonucleotide typically comprises a region of nucleotide sequence that hybridizes under stringent conditions to at least about 12. 25, 50, 100, 150, 200, 250, 300, 350 or 400 or more consecutive sense strand nucleotide sequence of SEQ ID NO:1; or an anti-sense strand nucleotide sequence of SEQ ID NO:1; or of a naturally occurring mutant of SEQ ID NO:1.

Probes based on the human ACPLX nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an ACPLX protein, such as by measuring a level of an ACPLX-encoding nucleic acid in a sample of cells from a subject e.g., detecting ACPLX mRNA levels or determining whether a genomic ACPLX gene has been mutated or deleted.

A "polypeptide having a biologically active portion of ACPLX" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of ACPLX" can be prepared by isolating a portion of SEQ ID NO:1 that encodes a polypeptide having an ACPLX biological activity (biological activities of the ACPLX proteins are described below), expressing the encoded portion of ACPLX protein (e.g., by recombinant expression in vitro) and assessing the activity of the encoded portion of ACPLX. For example, a nucleic acid fragment encoding a biologically active portion of ACPLX can optionally include an ATP-binding domain. In another embodiment, a nucleic acid fragment encoding a biologically active portion of ACPLX includes one or more regions.

ACPLX Variants

The invention further encompasses nucleic acid molecules that differ from the nucleotide sequences shown in SEQ ID NO:1 due to the degeneracy of the genetic code. These nucleic acids thus encode the same ACPLX protein as that encoded by the nucleotide sequence shown in SEQ ID NO:1, e.g., the polypeptide of SEQ ID NO:2. In another embodiment, an isolated nucleic acid molecule of the invention has a nucleotide sequence encoding a protein having an amino acid sequence shown in SEQ ID NO:2.

In addition to the human ACPLX nucleotide sequence shown in SEQ ID NO:1, it will be appreciated by those skilled in the art that DNA sequence polymorphisms that lead to changes in the amino acid sequences of ACPLX may exist within a population (e.g., the human population). Such genetic polymorphism in the ACPLX gene may exist among individuals within a population due to natural allelic variation. As used herein, the terms "gene" and "recombinant gene" refer to nucleic acid molecules comprising an open reading frame encoding an ACPLX protein, preferably a mammalian ACPLX protein. Such natural allelic variations can typically result in 1–5% variance in the nucleotide sequence of the ACPLX gene. Any and all such nucleotide variations and resulting amino acid polymorphisms in ACPLX that are the result of natural allelic variation and that do not alter the functional activity of ACPLX are intended to be within the scope of the invention.

Moreover, nucleic acid molecules encoding ACPLX proteins from other species, and thus that have a nucleotide sequence that differs from the human sequence of SEQ ID NO:1 are intended to be within the scope of the invention. Nucleic acid molecules corresponding to natural allelic variants and homologues of the ACPLX cDNAs of the invention can be isolated based on their homology to the human ACPLX nucleic acids disclosed herein using the human cDNAs, or a portion thereof, as a hybridization probe according to standard hybridization techniques under stringent hybridization conditions. For example, a soluble human ACPLX cDNA can be isolated based on its homology to human membrane-bound ACPLX. Likewise, a membrane-bound human ACPLX cDNA can be isolated based on its homology to soluble human ACPLX.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1. In another embodiment, the nucleic acid is at least 10, 25, 50, 100, 250, 500 or 750 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding ACPLX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM T ris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO:1 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:1, or fragments, analogs or derivatives thereof, under conditions of moderate stringency is provided. A non-limiting example of moderate stringency hybridization conditions are hybridization in 6×SSC, 5× Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Krlegler, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NO:1, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, *Proc Natl Acad Sci USA* 78: 6789–6792.

Conservative Mutations

In addition to naturally-occurring allelic variants of the ACPLX sequence that may exist in the population, the skilled artisan will further appreciate that changes can be introduced by mutation into the nucleotide sequence of SEQ ID NO:1, thereby leading to changes in the amino acid sequence of the encoded ACPLX protein, without altering the functional ability of the ACPLX protein. For example, nucleotide substitutions leading to amino acid substitutions at "non-essential" amino acid residues can be made in the sequence of SEQ ID NO:1. A "non-essential" amino acid residue is a residue that can be altered from the wild-type sequence of ACPLX without altering the biological activity, whereas an "essential" amino acid residue is required for biological activity. For example, amino acid residues that are conserved among the ACPLX proteins of the present invention, are predicted to be particularly unamenable to alteration.

In addition, amino acid residues that are conserved among ACPLX members, as indicated by the alignments presented as FIGS. 3A–C and 4, are predicted to be less amenable to alteration. For example, ACPLX proteins of the present invention can contain at least one domain that is a typically conserved region in ACPLX members, i.e., carboxypeptidase family proteins, and ACPLX homologs. As such, these conserved domains are not likely to be amenable to mutation. Other amino acid residues, however, (e.g., those that are not conserved or only semi-conserved among members of the ACPLX proteins) may not be as essential for activity and thus are more likely to be amenable to alteration.

Another aspect of the invention pertains to nucleic acid molecules encoding ACPLX proteins that contain changes in amino acid residues that are not essential for activity. Such ACPLX proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 75% homologous to the amino acid sequence of SEQ ID NO:2. Preferably, the protein encoded by the nucleic acid is at least about 80% homologous to SEQ ID NO:2, more preferably at least about 90%, 95%, 98%, and most preferably at least about 99% homologous to SEQ ID NO:2.

An isolated nucleic acid molecule encoding an ACPLX protein homologous to the protein of SEQ ID NO:2 can be created by introducing one or more nucleotide substitutions, additions or deletions into the nucleotide sequence of SEQ ID NO:1, such that one or more amino acid substitutions, additions or deletions are introduced into the encoded protein.

Mutations can be introduced into the nucleotide sequence of SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in ACPLX is replaced with another amino acid residue from the same side chain family. Alternatively, in another embodiment, mutations can be introduced randomly along all or part of an ACPLX coding sequence, such as by saturation mutagenesis, and the resultant mutants can be screened for ACPLX biological activity to identify mutants that retain activity. Following mutagenesis of SEQ ID NO:1, 3, 5, 7, 9, 11, 13, 15, 17, 19, 21, or 23, the encoded protein can be expressed by any recombinant technology known in the art and the activity of the protein can be determined.

In one embodiment, a mutant ACPLX protein can be assayed for (1) the ability to form protein:protein interactions with other ACPLX proteins, other cell-surface proteins, or biologically active portions thereof, (2) complex formation between a mutant ACPLX protein and an ACPLX receptor; (3) the ability of a mutant ACPLX protein to bind to an intracellular target protein or biologically active portion thereof; (e.g., avidin proteins); (4) the ability to bind BRA protein; or (5) the ability to specifically bind an anti-ACPLX protein antibody.

Antisense ACPLX Nucleic Acids

Another aspect of the invention pertains to isolated antisense nucleic acid molecules that are hybridizable to or complementary to the nucleic acid molecule comprising the nucleotide sequence of SEQ ID NO:1, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire ACPLX coding strand, or to only a portion thereof. Nucleic acid molecules encoding fragments, homologs, derivatives and analogs of an ACPLX protein of SEQ ID NO:2, or antisense nucleic acids complementary to an ACPLX nucleic acid sequence of SEQ ID NO:1 are additionally provided.

In one embodiment, an antisense nucleic acid molecule is antisense to a "coding region" of the coding strand of a nucleotide sequence encoding ACPLX. The term "coding region" refers to the region of the nucleotide sequence comprising codons which are translated into amino acid residues (e.g., the protein coding region of human ACPLX corresponds to SEQ ID NO:2). In another embodiment, the antisense nucleic acid molecule is antisense to a "noncoding region" of the coding strand of a nucleotide sequence encoding ACPLX. The term "noncoding region" refers to 5' and 3' sequences which flank the coding region that are not translated into amino acids (i.e., also referred to as 5' and 3' untranslated regions).

Given the coding strand sequences encoding ACPLX disclosed herein (e.g., SEQ ID NO:1), antisense nucleic acids of the invention can be designed according to the rules of Watson and Crick or Hoogsteen base pairing. The antisense nucleic acid molecule can be complementary to the entire coding region of ACPLX mRNA, but more preferably is an oligonucleotide that is antisense to only a portion of the coding or noncoding region of ACPLX mRNA. For example, the antisense oligonucleotide can be complementary to the region surrounding the translation start site of ACPLX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracl, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an ACPLX protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625–6641). The antisense nucleic acid molecule can also comprise a 2'-o-methylribonuclcotide (Inoue et al. (1987) *Nucleic Acids Res* 15: 6131–6148) or a chimeric RNA-DNA analogue (Inoue et al. (1987) *FEBS Lett* 215: 327–330).

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

ALCLPLX Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave ACPLX mRNA transcripts to thereby inhibit translation of ACPLX mRNA. A ribozyme having specificity for an ACPLX-encoding nucleic acid can be designed based upon the nucleotide sequence of an ACPLX DNA disclosed herein (i.e., SEQ ID NO:1). For example, a derivative of a Tetrahymena L-19 IVS RNA can be constructed in which the nucleotide sequence of the active site is complementary to the nucleotide sequence to be cleaved in an ACPLX-encoding mRNA. See, e.g., Cech et al. U.S. Pat. No. 4,987,071; and Cech et al. U.S. Pat. No. 5,116,742. Alternatively, ACPLX mRNA can be used to select a catalytic RNA having a specific ribonuclease activity from a pool of RNA molecules. See, e.g., Bartel et al., (1993) *Science* 261:1411–1418.

Alternatively, ACPLX gene expression can be inhibited by targeting nucleotide sequences complementary to the regulatory region of the ACPLX (e.g., the ACPLX promoter and/or enhancers) to form triple helical structures that prevent transcription of the ACPLX gene in target cells. See generally, Helene. (1991) *Anticancer Drug Des*. 6: 569–84; Helene. et al. (1992) *Ann. N.Y Acad. Sci*. 660:27–36; and Maher (1992) *Bioassays* 14: 807–15.

In various embodiments, the nucleic acids of ACPLX can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above, Perry-O'Keefe et al. (1996) *PNAS* 93: 14670–675.

PNAs of ACPLX can be used in therapeutic and diagnostic applications. For example, PNAs can be used as antisense or antigene agents for sequence-specific modulation of gene expression by, e.g., inducing transcription or translation arrest or inhibiting replication. PNAs of ACPLX can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above). In another embodiment, PNAs of ACPLX can be modified, e.g, to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of ACPLX can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A*. 86:6553–6556; Lemaitre et al., 1987, *Proc. Natl. Acad. Sci.* 84:648–652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

ACPLX Polypeptides

An ACPLX polypeptide of the invention includes the ACPLX-like protein whose sequence is provided in SEQ ID NO:2. The invention also includes a mutant or variant protein any of whose residues may be changed from the corresponding residue shown in SEQ ID NO:2 while still encoding a protein that maintains its ACPLX-like activities and physiological functions, or a functional fragment thereof. In some embodiments, up to 20% or more of the residues may be so changed in the mutant or variant protein. In some embodiments, the ALCLPLX polypeptide according to the invention is a mature polypeptide.

In general, an ACPLX-like variant that preserves ACPLX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated ACPLX proteins, and biologically active portions thereof, or derivatives, fragments, analogs or homologs thereof. Also provided are polypeptide fragments suitable for use as immunogens to raise anti-ACPLX antibodies. In one embodiment, native ACPLX proteins can be isolated from cells or tissue sources by an appropriate purification scheme using standard protein purification techniques. In another embodiment, ACPLX proteins are produced by recombinant DNA techniques. Alternative to recombinant expression, an ACPLX protein or polypeptide can be synthesized chemically using standard peptide synthesis techniques.

An "isolated" or "purified" protein or biologically active portion thereof is substantially free of cellular material or other contaminating proteins from the cell or tissue source from which the ACPLX protein is derived, or substantially free from chemical precursors or other chemicals when chemically synthesized. The language "substantially free of cellular material" includes preparations of ACPLX protein in which the protein is separated from cellular components of the cells from which it is isolated or recombinantly produced. In one embodiment, the language "substantially free of cellular material" includes preparations of ACPLX protein having less than about 30% (by dry weight) of non-ACPLX protein (also referred to herein as a "contaminating protein"), more preferably less than about 20% of non-ACPLX protein, still more preferably less than about 10% of non-ACPLX protein, and most preferably less than about 5% non-ACPLX protein. When the ACPLX protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of ACPLX protein in which the protein is separated from chemical precursors or other chemicals that are involved in the synthesis of the protein. In one embodiment, the language "substantially free of chemical precursors or other chemicals" includes preparations of ACPLX protein having less than about 30% (by dry weight) of chemical precursors or non-ACPLX chemicals, more preferably less than about 20% chemical precursors or non-ACPLX chemicals, still more preferably less than about 10% chemical precursors or non-ACPLX chemicals, and most preferably less than about 5% chemical precursors or non-ACPLX chemicals.

Biologically active portions of an ACPLX protein include peptides comprising amino acid sequences sufficiently homologous to or derived from the amino acid sequence of the ACPLX protein, e.g., the amino acid sequence shown in SEQ ID NO:2 that include fewer amino acids than the full length ACPLX proteins, and exhibit at least one activity of an ACPLX protein. Typically, biologically active portions comprise a domain or motif with at least one activity of the ACPLX protein. A biologically active portion of an ACPLX protein can be a polypeptide which is, for example, 10, 25, 50, 100 or more amino acids in length.

A biologically active portion of an ACPLX protein of the present invention may contain at least one of the above-identified domains conserved between the ACPLX proteins. Moreover, other biologically active portions, in which other regions of the protein are deleted, can be prepared by recombinant techniques and evaluated for one or more of the functional activities of a native ACPLX protein.

In an embodiment, the ACPLX protein has an amino acid sequence shown in SEQ ID NO:2. In other embodiments, the ACPLX protein is substantially homologous to SEQ ID NO:2 and retains the functional activity of the protein of SEQ ID NO:2, yet differs in amino acid sequence due to natural allelic variation or mutagenesis, as described in detail below. Accordingly, in another embodiment, the ACPLX protein is a protein that comprises an amino acid sequence at least about 45% homologous to the amino acid sequence of SEQ ID NO:2 and retains the functional activity of the ACPLX proteins of SEQ ID NO:2.

Determining Homology Between Two or More Sequence

To determine the percent homology of two amino acid sequences or of two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48:443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Chimeric and Fusion Proteins

The invention also provides ACPLX chimeric or fusion proteins. As used herein, an ACPLX "chimeric protein" or "fusion protein" comprises an ACPLX polypeptide operatively linked to a non-ACPLX polypeptide. An "ACPLX polypeptide" refers to a polypeptide having an amino acid sequence corresponding to ACPLX, whereas a "non-ACPLX polypeptide" refers to a polypeptide having an amino acid sequence corresponding to a protein that is not substantially homologous to the ACPLX protein, e.g., a protein that is different from the ACPLX protein and that is derived from the same or a different organism. Within an ACPLX fusion protein the ACPLX polypeptide can correspond to all or a portion of an ACPLX protein. In one embodiment, an ACPLX fusion protein comprises at least one biologically active portion of an ACPLX protein. In another embodiment, an ACPLX fusion protein comprises at least two biologically active portions of an ACPLX protein. Within the fusion protein, the term "operatively linked" is intended to indicate that the ACPLX polypeptide and the non-ACPLX polypeptide are fused in-frame to each other. The non-ACPLX polypeptide can be fused to the N-terminus or C-terminus of the ACPLX polypeptide.

For example, in one embodiment an ACPLX fusion protein comprises an ACPLX polypeptide operably linked to the extracellular domain of a second protein. Such fusion proteins can be further utilized in screening assays for compounds that modulate ACPLX activity (such assays are described in detail below).

In another embodiment, the fusion protein is a GST-ACPLX fusion protein in which the ACPLX sequences are fused to the C-terminus of the GST (i.e., glutathione S-transferase) sequences. Such fusion proteins can facilitate the purification of recombinant ACPLX.

In yet another embodiment, the fusion protein is an ACPLX protein containing a heterologous signal sequence at its N-terminus. For example, the native ACPLX signal sequence (i.e., amino acids 1 to of SEQ ID NO:2) can be removed and replaced with a signal sequence from another protein. In certain host cells (e.g., mammalian host cells), expression and/or secretion of ACPLX can be increased through use of a heterologous signal sequence.

In another embodiment, the fusion protein is an ACPLX-immunoglobulin fusion protein in which the ACPLX sequences comprising one or more domains are fused to sequences derived from a member of the immunoglobulin protein family. The ACPLX-immunoglobulin fusion proteins of the invention can be incorporated into pharmaceutical compositions and administered to a subject to inhibit an interaction between an ACPLX ligand and an ACPLX protein on the surface of a cell, to thereby suppress ACPLX-mediated signal transduction in vivo. In one nonlimiting example, a contemplated ACPLX ligand of the invention is the ACPLX receptor. The ACPLX-immunoglobulin fusion proteins can be used to affect the bioavailability of an ACPLX cognate ligand. Inhibition of the ACPLX ligand/ACPLX interaction may be useful therapeutically for both the treatment of proliferative and differentiative disorders, as well as modulating (e.g., promoting or inhibiting) cell survival. Moreover, the ACPLX-immunoglobulin fusion proteins of the invention can be used as immunogens to produce anti-ACPLX antibodies in a subject, to purify ACPLX ligands, and in screening assays to identify molecules that inhibit the interaction of ACPLX with an ACPLX ligand.

An ACPLX chimeric or fusion protein of the invention can be produced by standard recombinant DNA techniques. For example. DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example. Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). AN ACPLX-encoding nucleic acid can be cloned into such an expression vector such that the fusion moiety is linked in-frame to the ACPLX protein.

ACPLX Agonists and Antagonists

The present invention also pertains to variants of the ACPLX proteins that function as either ACPLX agonists (mimetics) or as ACPLX antagonists. Variants of the ACPLX protein can be generated by mutagenesis, e.g., discrete point mutation or truncation of the ACPLX protein. An agonist of the ACPLX protein can retain substantially the same, or a subset of, the biological activities of the naturally occurring form of the ACPLX protein. An antagonist of the ACPLX protein can inhibit one or more of the activities of the naturally occurring form of the ACPLX protein by, for example, competitively binding to a downstream or upstream member of a cellular signaling cascade which includes the ACPLX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the ACPLX proteins.

Variants of the ACPLX protein that function as either ACPLX agonists (mimetics) or as ACPLX antagonists can be identified by screening combinatorial libraries of mutants, e.g, truncation mutants, of the ACPLX protein for ACPLX protein agonist or antagonist activity. In one embodiment, a variegated library of ACPLX variants is generated by combinatorial mutagenesis at the nucleic acid level and is encoded by a variegated gene library. A variegated library of ACPLX variants can be produced by, for example, enzymatically ligating a mixture of synthetic oligonucleotides into gene sequences such that a degenerate set of potential ACPLX sequences is expressible as individual polypeptides, or alternatively, as a set of larger fusion proteins (e.g., for phage display) containing the set of ACPLX sequences therein. There are a variety of methods which can be used to produce libraries of potential ACPLX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential ACPLX sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the ACPLX protein coding sequence can be used to generate a variegated population of ACPLX fragments for screening and subsequent selection of variants of an ACPLX protein. In one embodiment, a library of coding sequence fragments can be generated by treating a double stranded PCR fragment of an ACPLX coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with SI nuclease, and ligating the resulting fragment library into an expression vector. By this method, an expression library can be derived which encodes N-terminal and internal fragments of various sizes of the ACPLX protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of ACPLX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify ACPLX variants (Arkin and Yourvan (1992) PNAS 89:7811–7815; Delgrave et al. (1993) Protein Engineering 6:327–331).

ACPLX Antibodies

Also included in the invention are antibodies to ACPLX proteins, or fragments of ACPLX proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated ACPLX-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO:2, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of ACPLX-related protein that is located on the surface of the protein, e g., a hydrophilic region. A hydrophobicity analysis of the human ACPLX-related protein sequence will indicate which regions of an ACPLX-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and Corynebacterium parvum, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromycloma cell lines also have been described for the production of human monoclonal antibodies (Kozbor, *J. Immunol.*, 133:3001 (1984); Brodeur et al., Monoclonal Antibody Production Techniques and Applications, Marcel Dekker. Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subdlones can be isolated or purified from the culture medium or aseites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F (ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann ct al., *Nature*, 332:3–227 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances. Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986: Riechmann et al., 1988; and Presta, *Curr. Op. Struct. Biol.*, 2:593–596 (1992)).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in Marks et al. (*Bio/Technology* 10, 779–783 (1992)); Lonberg et al. (*Nature* 368 856–859(1994)); Morrison (*Nature* 368, 812–13 (1994)); Fishwild et al, (*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829. published May 13, 1993, and in Traunecker et al., 1991 EMBO J., 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217–225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (Fc R), such as Fc RI (CD64), Fc RII (CD32) and Fc RIII (CD16) as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fc regions and can thereby have enhanced complement lysis and ADCC capabilities. See Stevenson et al., Anti-Cancer Drug Desin, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bisactive fluorine compounds (such as 1,5-difluoro-2,4-dinitrobenzene). For example, a ricin immunotoxin can be prepared as described in Vitetta et al., Science, 23 8: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

ACPLX Recombinant Expression Vectors and Host Cells

Another aspect of the invention pertains to vectors, preferably expression vectors, containing a nucleic acid encoding an ACPLX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., ACPLX proteins, mutant forms of ACPLX proteins, fusion proteins, etc.).

The recombinant expression vectors of the invention can be designed for expression of ACPLX proteins in prokaryotic or eukaryotic cells. For example, ACPLX proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fuision or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fulse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to protcolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the ACPLX expression vector is a yeast expression vector. Examples of vectors for expression in yeast *Saccharomyces cerivisae* include pYepSec1 (Baldari, et al., 1987. *EMBO. J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, ACPLX can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banerji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter, U.S. Pat. No. 4,873, 316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to ACPLX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, ACPLX protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, el cal. (MOLECULAR CLONING: A LABORATORY MANUAL. 2nd ed., Cold Spring Harbor Laboratory, Cold Spring Harbor laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding ACPLX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) ACPLX protein. Accordingly, the invention further provides methods for producing ACPLX protein using the host cells of the invention. In one embodiment, the method comprises culturing the host cell of invention (into which a recombinant expression vector encoding ACPLX protein has been introduced) in a suitable medium such that ACPLX protein is produced. In another embodiment, the method further comprises isolating ACPLX protein from the medium or the host cell.

Transgenic ACPLX Animals

The host cells of the invention can also be used to produce non-human transgenic animals. For example, in one embodiment, a host cell of the invention is a fertilized oocyte or an embryonic stem cell into which ACPLX protein-codin(g sequences have been introduced. Such host cells can then be used to create non-human transgenic animals in which exogenous ACPLX sequences have been introduced into their genome or homologous recombinant animals in which endogenous ACPLX sequences have been altered. Such animals are useful for studying the function and/or activity of ACPLX protein and for identifying and/or evaluating modulators of ACPLX protein activity. As used herein, a "transgenic animal" is a non-human animal, preferably a mammal, more preferably a redent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous ACPLX gene has been altered by homologous recombination between the endogenous gene and an exo(genous DNA molecule introduced into a cell of the animal, e.g., an embryonic cell of the animal, prior to development of the animal.

A transgenic animal of the invention can be created by introducing ACPLX-encoding nucleic acid into the male pronuclei of a fertilized oocyte (e.g., by microinjection, retroviral infection) and allowing the oocyte to develop in a pseudopregnant female foster animal. Sequences including SEQ ID NO:1 can be introduced as a transgene into the oenome of a non-human animal. Alternatively, a non-human homologue of the human ACPLX gene, such as a mouse ACPLX gene, can be isolated based on hybridization to the human ACPLX cDNA (described further supra) and used as a transgene. Intronic sequences and polyadenylation signals can also be included in the transgene to increase the efficiency of expression of the transgene. A tissue-specific regulatory sequence(s) can be operably-linked to the ACPLX transgene to direct expression of ACPLX protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the ACPLX transgene in its genome and/or expression of ACPLX mRNA in tissues or cells of the animals. A transgenic founder animal can then be used to breed additional animals carrying the transgene. Moreover, transgenic animals carrying a transgene-encoding ACPLX protein can further be bred to other transgenic animals carrying other transgenes.

To create a homologous recombinant animal, a vector is prepared which contains at least a portion of an ACPLX gene into which a deletion, addition or substitution has been introduced to thereby alter, e.g., functionally disrupt, the ACPLX gene. The ACPLX gene can be a human gene (e.g., the DNA of SEQ ID NO:1), but more preferably, is a non-human homologue of a human ACPLX gene. For example, a mouse homologue of human ACPLX gene of SEQ ID NO:1 can be used to construct a homologous recombination vector suitable for altering an endogenous ACPLX gene in the mouse genome. In one embodiment, the vector is designed such that, upon homologous recombination, the endogenous ACPLX gene is functionally disrupted (i.e., no longer encodes a functional protein; also referred to as a "knock out" vector).

Alternatively, the vector can be designed such that, upon homologous recombination, the endogenous ACPLX gene is mutated or otherwise altered but still encodes functional protein (e.g., the upstream regulatory region can be altered to thereby alter the expression of the endogenous ACPLX protein). In the homologous recombination vector, the altered portion of the ACPLX gene is flanked at its 5'- and 3'-termini by additional nucleic acid of the ACPLX gene to allow for homologous recombination to occur between the exogenous ACPLX gene carried by the vector and an endogenous ACPLX gene in an embryonic stem cell. The additional flanking ACPLX nucleic acid is of sufficient length for successful homologous recombination with the endogenous gene. Typically, several kilobases of flanking DNA (both at the 5'- and 3'-termini) are included in the vector. See, e.g., Thomas, et al., 1987. Cell 51: 503 for a description of homologous recombination vectors. The vector is ten introduced into an embryonic stem cell line (e.g., by electroporation) and cells in which the introduced ACPLX gene has homologously-recombined with the endogenous ACPLX gene are selected. See, e.g., Li, et al., 1992. Cell 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. Curr. Opin. Biotechnol. 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. Proc. Natl. Acad. Sci. USA 89: 6232–6236. Another example of a recombinase system is the FLP recombinase system of Saccharomyces cerevisiae. See, O'Gorman, et al., 1991. Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. Nature 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The ACPLX nucleic acid molecules, ACPLX proteins, and anti-ACPLX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al ., J. Biol. Chem., 257: 286–288 (1982) via a disulfide-interchange reaction. A chemotherapeutic agent (such as Doxorubicin) is optionally contained within the liposome. See Gabizon et al., J. National Cancer Inst., 81(19): 1484 (1989).

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syrinoeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an ACPLX protein or anti-ACPLX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Faston, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., 1993 *Proc. Natl. Acad. Sci. USA*, 90: 7889–7893. TIhe formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Screening and Detection Methods

The isolated nucleic acid molecules of the invention can be used to express ACPLX protein (e.g., via a recombinant expression vector in a host cell in gene therapy applications), to detect ACPLX mRNA (e.g., in a biological sample) or a genetic lesion in an ACPLX gene, and to modulate ACPLX activity, as described further, below. In addition, the ACPLX proteins can be used to screen drugs or compounds that modulate the ACPLX protein activity or expression as well as to treat disorders characterized by insufficient or excessive production of ACPLX protein or production of ACPLX protein forms that have decreased or aberrant activity compared to ACPLX wild-type protein (e.g. Anxiety disorders; CNS disorders where GABA neurotransmitters are involved; Diabetes (regulates insulin release); Obesity (binds and transport lipids); and Infectious Disease (possesses anti-microbial activity). In addition, the anti-ACPLX antibodies of the invention can be used to detect and isolate ACPLX proteins and modulate ACPLX activity.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to ACPLX proteins or have a stimulatory or inhibitory effect on, e.g., ACPLX protein expression or ACPLX protein activity. The invention also includes compounds identified in the screening assays described herein.

In one embodiment, the invention provides assays for screening candidate or test compounds which bind to or modulate the activity of the membrane-bound form of an ACPLX protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. USA*. 90: 6909; Erb, et al., 1994. *Proc. Natl. Acad. Sci. USA*. 91: 11422; Zuckermann, et al., 1994. *J. Med. Chem*. 37: 2678; Cho, et al., 1993. *Science* 261: 1303; Carrell, et al., 1994. *Angew. Chem. Int. Ed. Engl*. 33: 2059; Carell, et al., 1994. *Angew. Chem. Int. Ed. Engl*. 33: 2061; and Gallop, et al., 1994. *J. Med. Chem*. 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No. 5,233,409), plasmids (Cull, et al., 1992. *Proc. Natl. Acad Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. USA*. 87: 6378–6382; Felici, 1991. *J. Mol. Biol*. 222: 301–310; Ladner, U.S. Pat. No. 5,233,409.).

In one embodiment, an assay is a cell-based assay in which a cell which expresses a membrane-bound form of ACPLX protein, or a biologically-active portion thereof, on the cell surface is contacted with a test compound and the ability of the test compound to bind to an ACPLX protein determined. The cell, for example, can of mammalian origin or a yeast cell. Determining the ability of the test compound to bind to the ACPLX protein can be accomplished, for example, by coupling the test compound with a radioisotope or enzymatic label such that binding of the test compound to the ACPLX protein or biologically-active portion thereof can be determined by detecting the labeled compound in a complex. For example, test compounds can be labeled with $^{125}I$, $^{35}S$, $^{14}C$, or $^3H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of ACPLX protein, or a biologically-active portion thereof, on the cell surface with a known compound which binds ACPLX to form an assay mixture, contacting the assay mixture with a test compound, and determining the ability of the test compound to interact with an ACPLX protein, wherein determining the ability of the test compound to interact with an ACPLX protein comprises determining the ability of the test compound to preferentially bind to ACPLX protein or a biologically-active portion thereof as compared to the known compound.

In another embodiment, an assay is a cell-based assay comprising contacting a cell expressing a membrane-bound form of ACPLX protein, or a biologically-active portion thereof, on the cell surface with a test compound and determining the ability of the test compound to modulate (e.g., stimulate or inhibit) the activity of the ACPLX protein or biologically-active portion thereof. Determining the ability of the test compound to modulate the activity of ACPLX or a biologically-active portion thereof can be accomplished, for example, by determining the ability of the ACPLX protein to bind to or interact with an ACPLX target molecule. As used herein, a "target molecule" is a molecule with which an ACPLX protein binds or interacts in nature, for example, a molecule on the surface of a cell which expresses an ACPLX interacting protein, a molecule on the surface of a second cell, a molecule in the extracellular milieu, a molecule associated with the internal surface of a cell membrane or a cytoplasmic molecule. An ACPLX target molecule can be a non-ACPLX molecule or an ACPLX protein or polypeptide of the invention. In one embodiment, an ACPLX target molecule is a component of a signal transduction pathway that facilitates transduction of an extracellular signal (e.g. a signal generated by binding of a compound to a membrane-bound ACPLX molecule) through the cell membrane and into the cell. The target, for example, can be a second intercellular protein that has catalytic activity or a protein that facilitates the association of downstream signaling molecules with ACPLX.

Determining the ability of the ACPLX protein to bind to or interact with an ACPLX target molecule can be accomplished by one of the methods described above for determining direct binding. In one embodiment, determining the ability of the ACPLX protein to bind to or interact with an ACPLX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising an ACPLX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting an ACPLX protein or biologically-active portion thereof with a test compound and determining the ability of the test compound to bind to the ACPLX protein or biologically-active portion thereof. Binding of the test compound to the ACPLX protein can be determined either directly or indirectly as described above. In one such embodiment, the assay comprises contacting the ACPLX protein or biologically-active portion thereof with a known compound which binds ACPLX to form an assay mixture, contacting the assay mixture with a test compound, and determining the ability of the test compound to interact with an ACPLX protein, wherein determining the ability of the test compound to interact with an ACPLX protein comprises determining the ability of the test compound to preferentially bind to ACPLX or biologically-active portion thereof as compared to the known compound.

In still another embodiment, an assay is a cell-free assay comprising contacting ACPLX protein or biologically-active portion thereof with a test compound and determining the ability of the test compound to modulate (e.g. stimulate or inhibit) the activity of the ACPLX protein or biologically-active portion thereof. Determining the ability of the test compound to modulate the activity of ACPLX can be accomplished, for example, by determining the ability of the ACPLX protein to bind to an ACPLX target molecule by one of the methods described above for determining direct binding. In an alternative embodiment, determining the ability of the test compound to modulate the activity of ACPLX protein can be accomplished by determining the ability of the ACPLX protein further modulate an ACPLX target molecule. For example, the catalytic/enzymatic activity of the target molecule on an appropriate substrate can be determined as described above.

In yet another embodiment, the cell-free assay comprises contacting the ACPLX protein or biologically-active portion thereof with a known compound which binds ACPLX protein to form an assay mixture, contacting the assay mixture with a test compound, and determining the ability of the test compound to interact with an ACPLX protein, wherein determining the ability of the test compound to interact with an ACPLX protein comprises determining the ability of the ACPLX protein to preferentially bind to or modulate the activity of an ACPLX target molecule.

The cell-free assays of the invention are amenable to use of both the soluble form or the membrane-bound form of ACPLX protein. In the case of cell-free assays comprising the membrane-bound form of ACPLX protein, it may be desirable to utilize a solubilizing agent such that the membrane-bound form of ACPLX protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the invention, it may be desirable to immobilize either ACPLX protein or its target molecule to facilitate separation of complexed from uncomplexed forms of one or both of the proteins, as well as to accommodate automation of the assay. Binding of a test compound to ACPLX protein, or interaction of ACPLX protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-ACPLX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or ACPLX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of ACPLX protein binding or activity determined using standard techniques.

Other techniques for immobilizing proteins on matrices can also be used in the screening assays of the invention. For example, either the ACPLX protein or its target molecule can be immobilized utilizing conjugation of biotin and streptavidin. Biotinylated ACPLX protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with ACPLX protein or target molecules, but which do not interfere with binding of the ACPLX protein to its target molecule, can be derivatized to the wells of the plate, and unbound target or ACPLX protein trapped in the wells by antibody conjugation. Methods for detecting such complexes, in addition to those described above for the GST-immobilized complexes, include immunodetection of complexes using antibodies reactive with the ACPLX protein or target molecule, as well as enzyme-linked assays that rely on detecting an enzymatic activity associated with the ACPLX protein or target molecule.

In another embodiment, modulators of ACPLX protein expression are identified in a method wherein a cell is contacted with a candidate compound and the expression of ACPLX mRNA or protein in the cell is determined. The level of expression of ACPLX mRNA or protein in the presence of the candidate compound is compared to the level of expression of ACPLX mRNA or protein in the absence of the candidate compound. The candidate compound can then be identified as a modulator of ACPLX mRNA or protein expression based upon this comparison. For example, when expression of ACPLX mRNA or protein is greater (i.e., statistically significantly greater) in the presence of the candidate compound than in its absence, the candidate compound is identified as a stimulator of ACPLX mRNA or protein expression. Alternatively, when expression of ACPLX mRNA or protein is less (statistically significantly less) in the presence of the candidate compound than in its absence, the candidate compound is identified as an inhibitor of ACPLX mRNA or protein expression. The level of ACPLX mRNA or protein expression in the cells can be determined by methods described herein for detecting ACPLX mRNA or protein.

In yet another aspect of the invention, the ACPLX proteins can be used as "bait proteins" in a two-hybrid assay or three hybrid assay (see, e.g., U.S. Pat. No. 5,283,317; Zervos, et al., 1993. *Cell* 72: 223–232; Madura, et al., 1993. *J. Biol. Chem.* 268: 12046–12054; Bartel, et al., 1993. *Biotechniques* 14: 920–924; Iwabuchi, et al., 1993. *Oncogene* 8: 1693–1696; and Brent WO 94/10300), to identify other proteins that bind to or interact with ACPLX ("ACPLX-binding proteins" or "ACPLX-bp") and modulate ACPLX activity. Such ACPLX-binding proteins are also likely to be involved in the propagation of signals by the ACPLX proteins as, for example, upstream or downstream elements of the ACPLX pathway.

The two-hybrid system is based on the modular nature of most transcription factors, which consist of separable DNA-binding and activation domains. Briefly, the assay utilizes two different DNA constructs. In one construct, the gene that codes for ACPLX is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an ACPLX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with ACPLX.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) identify an individual from a minute biological sample (tissue typing); and (ii) aid in forensic identification of a biological sample. Some of these applications are described in the subsections, below.

Tissue Typing

The ACPLX sequences of the invention can be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the ACPLX sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The ACPLX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NO:1, 3, 5, 7, or 9, are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining ACPLX protein and/or nucleic acid expression as well as ACPLX activity, in the context of a biological sample (e.g., blood, serum, cells, tissue) to thereby determine whether an individual is afflicted with a disease or disorder, or is at risk of developing a disorder, associated with aberrant ACPLX expression or activity. The invention also provides for prognostic (or predictive) assays for determining whether an individual is at risk of developing a disorder associated with ACPLX protein, nucleic acid expression or activity. For example, mutations in an ACPLX gene can be assayed in a biological sample. Such assays can be used for prognostic or predictive purpose to thereby prophylactically treat an individual prior to the onset of a disorder characterized by or associated with ACPLX protein, nucleic acid expression, or biological activity.

Another aspect of the invention provides methods for determining ACPLX protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of ACPLX in clinical trials.

These and other agents are described in further detail in the following sections.

Diagnostic Assays

An exemplary method for detecting the presence or absence of ACPLX in a biological sample involves obtaining a biological sample from a test subject and contacting the biological sample with a compound or an agent capable of detecting ACPLX protein or nucleic acid (e.g., mRNA, genomic DNA) that encodes ACPLX protein such that the presence of ACPLX is detected in the biological sample. An agent for detecting ACPLX mRNA or genomic DNA is a labeled nucleic acid probe capable of hybridizing to ACPLX mRNA or genomic DNA. The nucleic acid probe can be, for example, a full-length ACPLX nucleic acid, such as the nucleic acid of SEQ ID ID NO:1, or a portion thereof, such as an oligonucleotide of at least 15, 30, 50, 100, 250 or 500 nucleotides in length and sufficient to specifically hybridize under stringent conditions to ACPLX mRNA or genomic DNA. Other suitable probes for use in the diagnostic assays of the invention are described herein.

One agent for detecting ACPLX protein is an antibody capable of binding to ACPLX protein, preferably an antibody with a detectable label. Antibodies directed against a protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds.

An antibody specific for a protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect ACPLX mRNA, protein, or genomic DNA in a biological sample in vitro as well as in vivo. For example, in vitro techniques for detection of ACPLX mRNA include Northern hybridizations and in situ hybridizations. In vitro techniques for detection of ACPLX protein include enzyme linked immunosorbent assays (ELISAs), Western blots, immunoprecipitations, and immunofluorescence. In vitro techniques for detection of ACPLX genomic DNA include Southern hybridizations. Furthermore, in vivo techniques for detection of ACPLX protein include introducing into a subject a labeled anti-ACPLX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In one embodiment, the methods further involve obtaining a control biological sample from a control subject, contacting the control sample with a compound or agent capable of detecting ACPLX protein, mRNA, or genomic DNA, such that the presence of ACPLX protein, mRNA or genomic DNA is detected in the biological sample, and comparing the presence of ACPLX protein, mRNA or genomic DNA in the control sample with the presence of ACPLX protein, mRNA or genomic DNA in the test sample.

The invention also encompasses kits for detecting the presence of ACPLX in a biological sample. For example, the kit can comprise: a labeled compound or agent capable of detecting ACPLX protein or mRNA in a biological sample; means for determining the amount of ACPLX in the sample; and means for comparing the amount of ACPLX in the sample with a standard. The compound or agent can be packaged in a suitable container. The kit can further comprise instructions for using the kit to detect ACPLX protein or nucleic acid.

Prognostic Assays

The diagnostic methods described herein can furthermore be utilized to identify subjects having or at risk of developing a disease or disorder associated with aberrant ACPLX expression or activity. For example, the assays described herein, such as the preceding diagnostic assays or the following assays, can be utilized to identify a subject having or at risk of developing a disorder associated with ACPLX protein, nucleic acid expression or activity. Alternatively, the prognostic assays can be utilized to identify a subject having or at risk for developing a disease or disorder. Thus, the invention provides a method for identifying a disease or disorder associated with aberrant ACPLX expression or activity in which a test sample is obtained from a subject and ACPLX protein or nucleic acid (e.g., mRNA, genomic DNA) is detected, wherein the presence of ACPLX protein or nucleic acid is diagnostic for a subject having or at risk of developing a disease or disorder associated with aberrant ACPLX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant ACPLX expression or activity. For example, such methods can be used to determine whether a subject can be effectively treated with an agent for a disorder. Thus, the invention provides methods for determining whether a subject can be effectively treated with an agent for a disorder associated with aberrant ACPLX expression or activity in which a test sample is obtained and ACPLX protein or nucleic acid is detected (e.g., wherein the presence of ACPLX protein or nucleic acid is diagnostic for a subject that can be administered the agent to treat a disorder associated with aberrant ACPLX expression or activity).

The methods of the invention can also be used to detect genetic lesions in an ACPLX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding an ACPLX-protein, or the misexpression of the ACPLX gene. For example, such genetic lesions can be detected by ascertaining the existence of at least one of: (i) a deletion of one or more nucleotides from an ACPLX gene; (ii) an addition of one or more nucleotides to an ACPLX gene; (iii) a substitution of one or more nucleotides of an ACPLX gene, (iv) a chromosomal rearrangement of an ACPLX gene; (v) an alteration in the level of a messenger RNA transcript of an ACPLX gene, (vi) aberrant modification of an ACPLX gene, such as of the methylation pattern of the genomic DNA, (vii) the presence of a non-wild-type splicing pattern of a messenger RNA transcript of an ACPLX gene, (viii) a non-wild-type level of an ACPLX protein, (ix) allelic loss of an ACPLX gene, and (x) inappropriate post-translational modification of an ACPLX protein. As described herein, there are a large number of assay techniques known in the art which can be used for detecting lesions in an ACPLX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. *Science* 241: 1077–1080; and Nakazawa, et al., 1994. *Proc. Natl. Acad. Sci. USA* 91: 360–364), the latter of which can be particularly useful for detecting point mutations in the ACPLX-gene (see, Abravaya, et al., 1995. *Nucl. Acids Res.* 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to an ACPLX gene under conditions such that hybridization and amplification of the ACPLX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see. Guatelli, et al., 1990. *Proc. Natl. Acad. Sci. USA* 87: 1874–1878), transcriptional amplification system (see, Kwoh, et al., 1989. *Proc. Natl. Acad. Sci. USA* 86: 1173–1177); Qβ Replicase (see, Lizardi, et al, 1988. *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an ACPLX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in ACPLX can be identified by hybridizing a sample and control nucleic acids, e.g., DNA or RNA, to high-density arrays containing hundreds or thousands of oligonucleotides probes. See, e.g., Cronin, et al., 1996. *Human Mutation* 7: 244–255; Kozal, et al., 1996. *Nat. Med.* 2: 753–759. For example, genetic mutations in ACPLX can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant geene.

In yet another embodiment, any of a variety of sequencing reactions known in the art can be used to directly sequence the ACPLX goene and detect mutations by comparing the sequence of the sample ACPLX with the corresponding wild-type (control) sequence. Examples of sequencing reactions include those based on techniques developed by Maxim and Gilbert, 1977. *Proc. Natl. Acad. Sci. USA* 74: 560 or Sangaer, 1977. *Proc. Natl. Acad. Sci. USA* 74: 5463. It is also contemplated that any of a variety of automated sequencing procedures can be utilized when performing the diagnostic assays (see, e.g., Naeve, et al., 1995. *Biotechniques* 19: 448), including sequencing by mass spetrometry (see, e.g., PCT International Publication No. WO 94/16101; Cohen, et al., 1996. *Adv. Chromatography* 36: 127–162; and Griffin, et al., 1993. *appl. Biochem. Biotechnol.* 38: 147–159).

Other methods for detecting mutations in the ACPLX gene include methods in which protection from cleavage agents is used to detect mismatched bases in RNA/RNA or RNA/DNA heteroduplexes. See, e.g., Myers, et al., 1985. *Science* 230: 1242. In general, the art technique of "mismatch cleavage" starts by providing heteroduplexes of formed by hybridizing (labeled) RNA or DNA containing the wild-type ACPLX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. *Proc. Natl. Acad. Sci. USA* 85: 4397; Saleeba, et al., 1992. *Methods Enzymol.* 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in ACPLX cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. *Carcinogenesis*

15: 1657–1662. According to an exemplary embodiment, a probe based on an ACPLX sequence, e.g., a wild-type ACPLX sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in ACPLX genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA*: 86: 2766; Cotton, 1993. *Mutat. Res.* 285: 125–144; Hayashi, 1992. *Genet. Anal. Tech. Appl.* 9: 73–79. Single-stranded DNA fragments of sample and control ACPLX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. *Trends Genet.* 7:5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. *Nature* 313: 495. When DGGE is used as the method of analysis, DNA will be modified to insure that it does not completely denature, for example by addina a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324: 163; Saiki, et al., 1989. *Proc. Natl. Acad. Sci. USA* 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization, see, e.g., Gibbs, et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it may be desirable to introduce a novel restriction site in the region of the mutation to create cleavage-based detection. See, e.g., Gasparini, et al., 1992. *Mol. Cell Probes* 6: 1. It is anticipated that in certain embodiments amplification may also be performed using Taq ligase for amplification. See, e.g., Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an ACPLX gene.

Furthermore, any cell type or tissue, preferably peripheral blood leukocytes, in which ACPLX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on ACPLX activity (e.g., ACPLX gene expression), as identified by a screening assay described herein can be administered to individuals to treat (prophylactically or therapeutically) disorders (e.g., cancer or immune disorders associated with aberrant ACPLX activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of ACPLX protein, expression of ACPLX nucleic acid, or mutation content of ACPLX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. Pharmacol. Physiol.*, 23: 983–985; Linder, 1997. *Clin. Chem.*, 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of ACPLX protein, expression of ACPLX nucleic acid, or mutation content of ACPLX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an ACPLX modulator, such as a modulator identified by one of the exemplary screening assays described herein.

Monitoring of Effects During Clinical Trials

Monitoring the influence of agents (e.g., drugs, compounds) on the expression or activity of ACPLX (e.g., the ability to modulate aberrant cell proliferation and/or differentiation) can be applied not only in basic drug screening, but also in clinical trials. For example, the effectiveness of an agent determined by a screening assay as described herein to increase ACPLX gene expression, protein levels, or upregulate ACPLX activity, can be monitored in clinical trails of subjects exhibiting decreased ACPLX gene expression, protein levels, or downregulated ACPLX activity. Alternatively, the effectiveness of an agent determined by a screening assay to decrease ACPLX gene expression, protein levels, or downregulate ACPLX activity, can be monitored in clinical trails of subjects exhibiting increased ACPLX gene expression, protein levels, or upregulated ACPLX activity. In such clinical trials, the expression or activity of ACPLX and, preferably, other genes that have been implicated in, for example, a cellular proliferation or immune disorder can be used as a "read out" or markers of the immune responsiveness of a particular cell.

By way of example, and not of limitation, genes, including ACPLX, that are modulated in cells by treatment with an agent (e.g., compound, drug or small molecule) that modulates ACPLX activity (e.g., identified in a screening assay as described herein) can be identified. Thus, to study the effect of agents on cellular proliferation disorders, for example, in a clinical trial, cells can be isolated and RNA prepared and analyzed for the levels of expression of ACPLX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of ACPLX or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an ACPLX protein, mRNA, or genomic DNA in the preadministration sample; (iii) obtaining one or more post-administration samples from the subject; (iv) detecting the level of expression or activity of the ACPLX protein, mRNA, or genomic DNA in the post-administration samples; (v) comparing the level of expression or activity of the ACPLX protein, mRNA, or genomic DNA in the pre-administration sample with the ACPLX protein, mRNA, or genomic DNA in the post administration sample or samples; and (vi) altering the administration of the agent to the subject accordingly. For example, increased administration of the agent may be desirable to increase the expression or activity of ACPLX to higher levels than detected, i.e., to increase the effectiveness of the agent. Alternatively, decreased administration of the agent may be desirable to decrease expression or activity of ACPLX to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant ACPLX expression or activity. These methods of treatment will be discussed more fully, below.

Disease and Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof, (ii) antibodies to an aforementioned peptide, (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endoggenous function of an aforementioned peptide by homologous recombination (see, e.g., Capecchi, 1989. *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof, or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant ACPLX expression or activity, by administering to the subject an agent that modulates ACPLX expression or at least one ACPLX activity. Subjects at risk for a disease that is caused or contributed to by aberrant ACPLX expression or activity can be identified by, for example, any or a combination of diagnostic or prognostic assays as described herein. Administration of a prophylactic agent can occur prior to the manifestation of symptoms characteristic of the ACPLX aberrancy, such that a disease or disorder is prevented or, alternatively, delayed in its progression. Depending upon the type of ACPLX aberrancy, for example, an ACPLX agonist or ACPLX antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating ACPLX expression or activity for therapeutic purposes. The modulatory method of the invention involves contacting a cell with an agent that modulates one or more of the activities of ACPLX protein activity associated with the cell. An agent that modulates ACPLX protein activity can be an agent as described herein, such as a nucleic acid or a protein, a naturally-occurring cognate ligand of an ACPLX protein, a peptide, an ACPLX peptidomimetic, or other small molecule. In one embodiment, the agent stimulates one or more ACPLX protein activity. Examples of such stimulatory agents include active ACPLX protein and a nucleic acid molecule encoding ACPLX that has been introduced into the cell. In another embodiment, the agent inhibits one or more ACPLX protein activity. Examples of such inhibitory agents include antisense ACPLX nucleic acid molecules and anti-ACPLX antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of an ACPLX protein or nucleic acid molecule. In one embodiment, the method involves administering an agent (e.g., an ag,ent identified by a screening assay described herein), or combination of agents that modulates (e.g., up-regulates or down-regulates) ACPLX expression or activity. In another embodiment, the method involves administering an ACPLX protein or nucleic acid molecule as therapy to compensate for reduced or aberrant ACPLX expression or activity.

Stimulation of ACPLX activity is desirable in situations in which ACPLX is abnormally downregulated and/or in which increased ACPLX activity is likely to have a beneficial effect. One example of such a situation is where a subject has a disorder characterized by aberrant cell proliferation and/or differentiation (e.g., cancer or immune associated disorders).

Another example of such a situation is where the subject has a gestational disease (e.g., preclampsia).

Antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand which may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for *in vivo* testing, any of the animal model system known in the art may be used prior to administration to human subjects.

The invention will be further illustrated using the following non-limiting examples.

EXAMPLE 1

Molecular Cloning of an ALCLPX Nucleic Acid ("AL035460A")

A nucleotide sequence (SEQ ID NO:1) shown in FIG. 1 encoding a polypeptide (SEQ ID NO:2) related to known carboxypeptidases was identified by assembling various regions of human genomic DNA. The assembled sequence was named AL035460A.

The SIGNALP secretory signal prediction algorithm predicts that the polypeptide (SEQ ID NO:2) encoded by AL035460A has a signal peptidase cleavage site between residues 20 and 21. Accordingly the predicted ORF corresponding to the mature form of the encoded AL035460A protein was cloned.

Oligonucleotide primers were designed to amplify the DNA segment corresponding to this protein using PCR. The forward primer included an in frame BglII restriction site, and the reverse primer contained an in frame XhoI restriction site. The following PCR primers were used:

AL035460A Forw:
CTCGTCAGATCTGCGCCCAGGAACTCGGTGCTGGGCCTCG (SEQ ID NO:3), and

AL-035460A Rev:
CTCGTCCTCGAGATCCTTCTGTCCCCTTAGCCGCTCC (SEQ ID NO:4).

PCR reactions were performed using a total of 5 ng human adult heart cDNA template, 1 microM of each of the AL035460A Forw and AL035460A Rev primers, 5 micromoles dNTP (Clontech Laboratories, Palo Alto Calif.) and 1 microliter of 50xAdvantage-HF 2 polymerase (Clontech Laboratories, Palo Alto Calif.) in 50 microliter volume. The following reaction conditions were used:

| a) 96° C. | 3 minutes |
| b) 96° C. | 30 seconds denaturation |
| c) 70° C. | 30 seconds, primer annealing. |
| d) 72° C. | 4 minute extension. |

Repeat steps b–d 10 times, decreasing the temperature of step c) by 1° C./cycle;

| e) 96° C. | 30 seconds denaturation |
| f) 60° C. | 30 seconds annealing |
| g) 72° C. | 4 minute extension |

Repeat steps e–g 25 times;

| h) 72° C. | 10 minutes final extension. |

A PCR product having the expected size, approximately 2.2 kbp, was isolated from an agarose gel and ligated to the vector pCR2.1 (Invitrogen, Carlsbad, Calif.). The cloned insert was sequenced using vector specific, M13 Forward(−40) and M 3 Reverse primers, as well as the following gene specific primers:

| AL035460A S1: | AGCCGGCTTGAGGCATCCAGC | (SEQ ID NO:5) |
| AL035460A S2: | GCTGGATGCCTCAAGCCGGCT | (SEQ ID NO:6), |
| AL035460A S3: | CCAGAAACTCCAGTGCTGAAC | (SEQ ID NO:7), |
| AL035460A S4: | GTTCAGCACTGGAGTTTCTGG | (SEQ ID NO:8), |
| AL035460A S5: | CAAGCCTGGGGAGCATGAGCTG | (SEQ ID NO:9), |
| AL035460A S6: | CAGCTCATGCTCCCCAGGCTTG | (SEQ ID NO:10), |
| AL035460A S7: | CAGGACGATGGGAAGGTGCCC | (SEQ ID NO:11), |
| AL035460A S8: | GGGCACCTTCCCATCGTCCTG | (SEQ ID NO:12), |
| AL035460A S9: | AGCATGAATGACTTCAGCTAC | (SEQ ID NO:13), |
| AL035460A S10: | GTAGCTGAAGTCATTCATGCT | (SEQ ID NO:14), |
| AL035460A S11: | GAGCTTGGGATTGCTGACGCT | (SEQ ID NO:15), | and

| AL035460A S12: | GCGTCAGCAATCCCAAGCTC | (SEQ ID NO:16). |

The sequence of the insert was verified as an open reading frame coding for the predicted AL035460A mature protein from residues 21 to 734. The clone was named pCR2.1-AL035460.

EXAMPLE 2

Construction of the Mammalian Expression Vector pCEP4/Sec

A vector, named pCEP4/Sec, for examining expression of ACPLX sequences in mammalian cells was constructed.

The pCEP4/Sec vector was constructed from pcDNA3.1-V5His (Invitrogen, Carlsbad, Calif.). The following oligonucleotide primers were designed to amplify a fragment from the expression vector pcDNA3.1-V5His expression vector.

pSec-V5-His Forward CTCGTCCTCGAGGGTAAGCCTATCCCTAAC (SEQ ID NO:17) and pSec-V5-His Reverse CTCGTCGGGCCCCTGATCAGCGGGTTTAAAC (SEQ ID NO:18)

The PCR product was digested with XhoI and ApaI and ligated into the XhoI/ApaI digested pSecTag2 B vector harboring an Ig kappa leader sequence (Invitrogen, Carlsbad Calif.). The correct structure of the resulting vector, pSecV5His, including an in-frame Ig-kappa leader and V5-His6 was verified by DNA sequence analysis. The vector pSecV5His was digested with PmeI and NheI to provide a fragment retaining the above elements in the correct frame. The PmeI-NheI fragment was ligated into the BamHI/Klenow and NheI treated vector pCEP4 (Invitrogen, Carlsbad, Calif.). The resulting vector was named pCEP4/Sec and includes an in-frame Ig kappa leader, a site for insertion of a clone of interest, V5 and His6 under control of the PCMV and/or the PT7 promoter. PCEP4/Sec is an expression vector that allows heterologous protein expression and secretion by fusing any protein to the Ig Kappa chain signal peptide. Detection and purification of the expressed protein are aided by the presence of the V5 epitope tag and 6xHis tag at the C-terminus (Invitrogen, Carlsbad, Calif.).

EXAMPLE 3

Expression of AL035460A in Human Embryonic Kidney 293 Cells

The 2.1 kb BglII-XhoI fragment containing the human AL035460A sequence was isolated from pCR2.1-AL035460A (see Example 2) and subcloned into BglII-XhoI digested pCEP4/Sec to generate the expression vector pCEP4/Sec-AL035460. The pCEP4/Sec-AL035460A vector was transfected into 293 cells using the LipofectaminePlus reagent following the manufacturer's instructions (Gibco/BRL, Rockville, Md.). The cell pellet and supernatant were harvested 72 hours after transfection and examined for AL035460A expression by Western blotting (reducing conditions) with an anti-V5 antibody. The molecular weight predicted for the mature fragment of hAL035460, including four amino acid residues encoded by the primers, is 80132 Da. FIG. 6 shows that a monomeric form of hAL035460A is expressed as a predominant band of 125 kDa protein secreted by 293 cells. The mature fragment of AL035460A is predicted to have six potential sites for N-glycosylation. The discrepancy between the predicted molecular weight and the observed value is ascribed to glycosylation of the protein, which retards its migration in the gel. In addition, several higher molecular weight bands indicate oligomerization of the secreted AL035460A protein.

EXAMPLE 4

Expression Analysis Using Clone AL035460A

The expression of sequences homologous to clone AL035460A was assessed in 41 normal and 55 tumor samples by real time quantitative PCR (TAQMAN®) performed on a Perkin-Elmer Biosystems ABI PRISM® 7700 Sequence Detection System. In Table BB, the following abbreviations are used:

ca.=carcinoma,

*=established from metastasis, met=metastasis, s cell var=small cell variant, non-s=non-sm=non-small, squam=squamous, pl.eff=pl effusion=pleural effusion, glio=glioma, astro=astrocytoma, and neuro=neuroblastoma.

TABLE III

Tissue Samples used in Expression Analysis.

| No. | Tissue Sample |
|---|---|
| 1 | Endothelial cells |
| 2 | Endothelial cells (treated) |
| 3 | Pancreas |
| 4 | Pancreatic ca. CAPAN 2 |
| 5 | Adipose |
| 6 | Adrenal gland |
| 7 | Thyroid |
| 8 | Salivary gland |
| 9 | Pituitary gland |
| 10 | Brain (fetal) |
| 11 | Brain (whole) |
| 12 | Brain (amygdala) |
| 13 | Brain (cerebellum) |
| 14 | Brain (hippocampus) |
| 15 | Brain (hypothalamus) |
| 16 | Brain (substantia nigra) |
| 17 | Brain (thalamus) |
| 18 | Spinal cord |
| 19 | CNS ca. (glio/astro) U87-MG |
| 20 | CNS ca. (glio/astro) U-118-MG |
| 21 | CNS ca. (astro) SW1783 |
| 22 | CNS ca.* (neuro; met) SK-N-AS |
| 23 | CNS ca. (astro) SF-539 |
| 24 | CNS ca. (astro) SNB-75 |
| 25 | CNS ca. (glio) SNB-19 |
| 26 | CNS ca. (glio) U251 |
| 27 | CNS ca. (glio) SF-295 |
| 28 | Heart |
| 29 | Skeletal muscle |
| 30 | Bone marrow |
| 31 | Thymus |
| 32 | Spleen |
| 33 | Lymph node |
| 34 | Colon (ascending) |
| 35 | Stomach |
| 36 | Small intestine |
| 37 | Colon ca. SW480 |
| 38 | Colon ca.* (SW480 met)SW620 |
| 39 | Colon ca. HT29 |
| 40 | Colon ca. HCT-116 |
| 41 | Colon ca. CaCo-2 |
| 42 | Colon ca. HCT-15 |
| 43 | Colon ca. HCC-2998 |
| 44 | Gastric ca.* (liver met) NCl-N87 |
| 45 | Bladder |
| 46 | Trachea |
| 47 | Kidney |
| 48 | Kidney (fetal) |
| 49 | Renal ca. 786-0 |
| 50 | Renal ca. A498 |
| 51 | Renal ca. RXF 393 |
| 52 | Renal ca. ACHN |
| 53 | Renal ca. UO-31 |
| 54 | Renal ca. TK-10 |
| 55 | Liver |
| 56 | Liver (fetal) |
| 57 | Liver ca. (hepatobfast) HepG2 |
| 58 | Lung |
| 59 | Lung (fetal) |
| 60 | Lung ca. (small cell) LX-1 |
| 61 | Lung ca. (small cell) NCl-H69 |
| 62 | Lung ca. (s. cell var.) SHP-77 |
| 63 | Lung ca. (large cell)NCl-H460 |
| 64 | Lung ca. (non-sm. cell) A549 |
| 65 | Lung ca. (non-s. cell) NCl-H23 |
| 66 | Lung ca (non-s. cell) HOP-62 |
| 67 | Lung ca. (non-s. cl) NCl-H522 |
| 68 | Lung ca. (squam.) SW 900 |
| 69 | Lung ca. (squam.) NCl-H596 |
| 70 | Mammary gland |
| 71 | Breast ca.* (pl. effusion) MCF-7 |
| 72 | Breast ca.* (pl. ef) MDA-MB-231 |
| 73 | Breast ca.* (pl. effusion) T47D |
| 74 | Breast ca. BT-549 |
| 75 | Breast ca. MDA-N |
| 76 | Ovary |
| 77 | Ovarian ca. OVCAR-3 |
| 78 | Ovarian ca. OVCAR-4 |
| 79 | Ovarian ca. OVCAR-5 |
| 80 | Ovarian ca. OVCAR-8 |
| 81 | Ovarian ca. IGROV-1 |
| 82 | Ovarian ca.* (ascites) SK-OV-3 |
| 83 | Myometrium |
| 84 | Uterus |
| 85 | Placenta |
| 86 | Prostate |
| 87 | Prostate ca.* (bone met)PC-3 |
| 88 | Testis |

TABLE III-continued

Tissue Samples used in Expression Analysis.

| No. | Tissue Sample |
|---|---|
| 89 | Melanoma Hs688(A).T |
| 90 | Melanoma* (met) Hs688(B).T |
| 91 | Melanoma UACC-62 |
| 92 | Melanoma M14 |
| 93 | Melanoma LOX IMVI |
| 94 | Melanoma* (met) SK-MEL-5 |
| 95 | Melanoma SK-MEL-28 |
| 96 | Melanoma UACC-257 |

96 RNA samples were analyzed. Expression was compared to a reference RNA. In particular, samples were normalized to β-actin and GAPDH. RNA (~50 ng total or ~1 ng polyA+) was converted to cDNA using the TAQMAN® Reverse Transcription Reagents Kit (PE Biosystems, Foster City, Calif.; cat # N808-0234) and random hexamers according to the manufacturer's protocol. Reactions were performed in 20 ul and incubated for 30 min. at 48° C. cDNA (5 ul) was then transferred to a separate plate for the TAQMAN® reaction using β-actin and GAPDH TAQMAN® Assay Reagents (PE Biosystems; cat. #'s 4310881E and 4310884E, respectively) and TAQMAN® universal PCR Master Mix (PE Biosystems; cat # 4304447) according to the manufacturer's protocol. Reactions were performed in 25 ul using the following parameters: 2 min. at 50° C.; 10 min. at 95° C.; 15 sec. at 95° C./1 min. at 60° C. (40 cycles). Results were recorded as CT values (cycle at which a given sample crosses a threshold level of fluorescence) using a log scale, with the difference in RNA concentration between two samples being represented as 2 to the power of delta CT. The average CT values obtained for β-actin and GAPDH were used to normalize RNA samples. The RNA sample generating the highest CT value required no further diluting, while all other samples were diluted relative to this sample according to their β-actin/GAPDH average CT values.

Normalized RNA (5 ul) was converted to cDNA and analyzed via TAQMAN® using One step RT-PCR Master Mix Reagents (PE Biosystems; cat. # 4309169) and gene-specific primers according to the manufacturer's instructions. Probes and primers were designed for the assay according to Perkin Elmer Biosystem's Primer Express Software package (version I for Apple Computer's Macintosh Power PC) using the sequence of cloneAL035460A as input. Two sets of primers (forward and reverse) and probe were developed, shown below.

Set Ag 86 targets the sequence 267–342.

Ag86 (F): 5'-GTCTGGAGTCCCTGCGAGTTT-3' (SEQ ID NO:19)

Ag86 (R): 5'-CGGTGTGGTCCAAGACCAA-3' (SEQ ID NO:20)

Ag86 (P): TET-5'-CTTGAGGCATCCAGCAGCCAGTCC-3'-TAMRA (SEQ ID NO:21)

Set Ag 86b targets the sequence 271–346.

AG 86(b) (F): 5'-GAGTCCCTGCGAGTTTCAGATAG-3' (SEQ ID NO:22)

AG 86(b) (R): 5'-GTCCTCGGTGTGGTCCAAGA-3' (SEQ ID NO:23)

AG 86(b) (P): TET-5'-TGAGGCATCCAGCAGCCAGTCCTTT-3'-TAMRA (SEQ ID NO:24)

Default settings were used for reaction conditions and the following parameters were set before selecting primers: primer concentration=250 nM, primer melting temperature ($T_m$) range=58°–60° C., primer optimal Tm=59° C., maximum primer difference=2° C., probe does not have 5' G, probe $T_m$ must be 10° C. greater than primer $T_m$, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM.

PCR conditions: Normalized RNA from each tissue and each cell line was spotted in each well of a 96 well PCR plate (Perkin Elmer Biosystems). PCR cocktails including two probes (ALCLPLX-specific and another gene-specific probe multiplexed with the ALCLPX probe) were set up using 1X TaqMan™ PCR Master Mix for the PE Biosystems 7700, with 5 mM MgC12, dNTPs (dA, G, C, U at 1:1:1:2 ratios), 0.25 U/ml AmpliTaq Gold™ (PE Biosystems), and 0.4 U/µl RNase inhibitor, and 0.25 U/µl reverse transcriptase. Reverse transcription was performed at 48° C. for 30 minutes followed by amplification/PCR cycles as follows: 95° C. 10 min, then 40 cycles of 95° C. for 15 seconds, 60° C. for 1 minute.

Figure 6B:
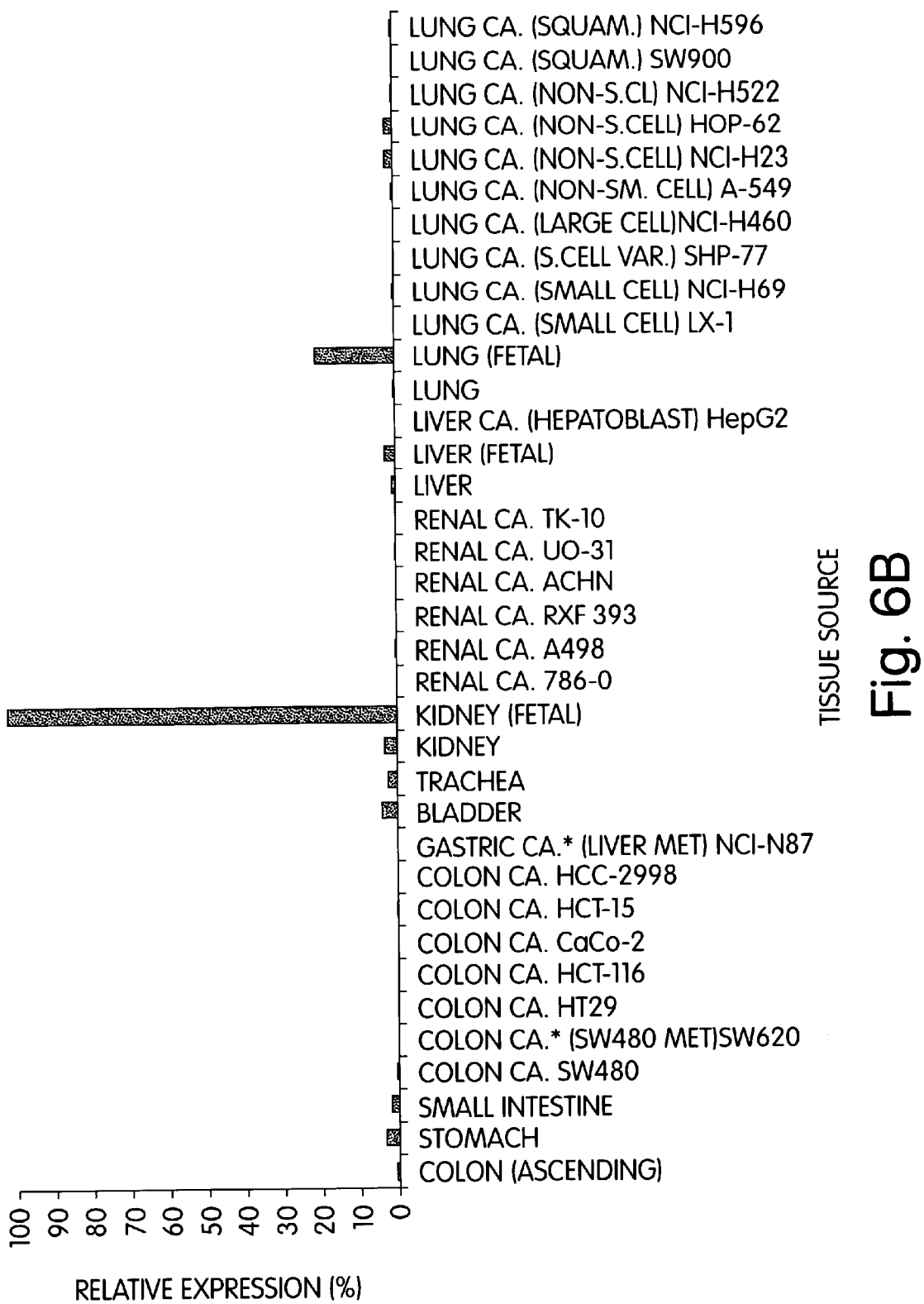
Figure 6C:
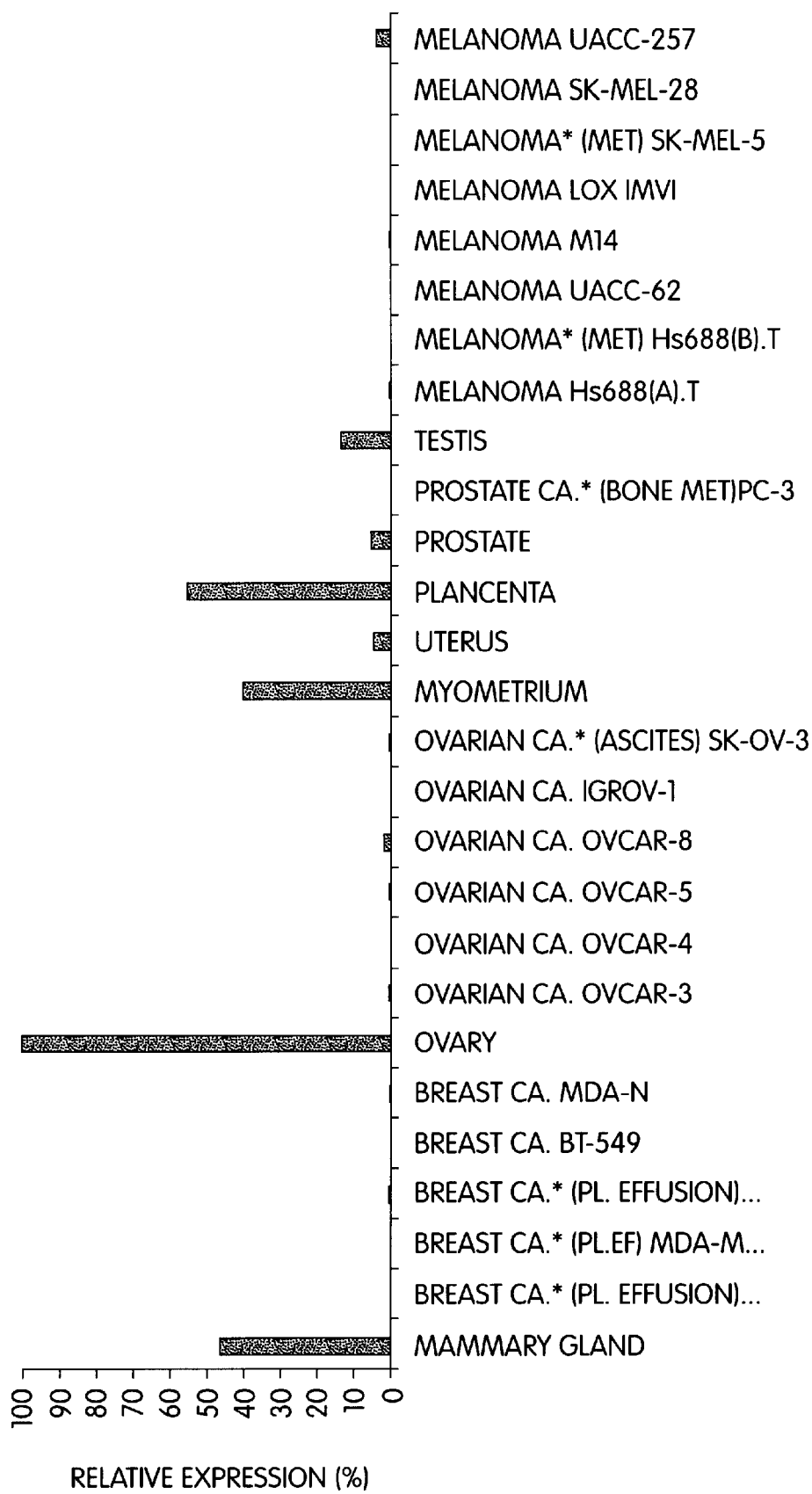
Figure 7C:
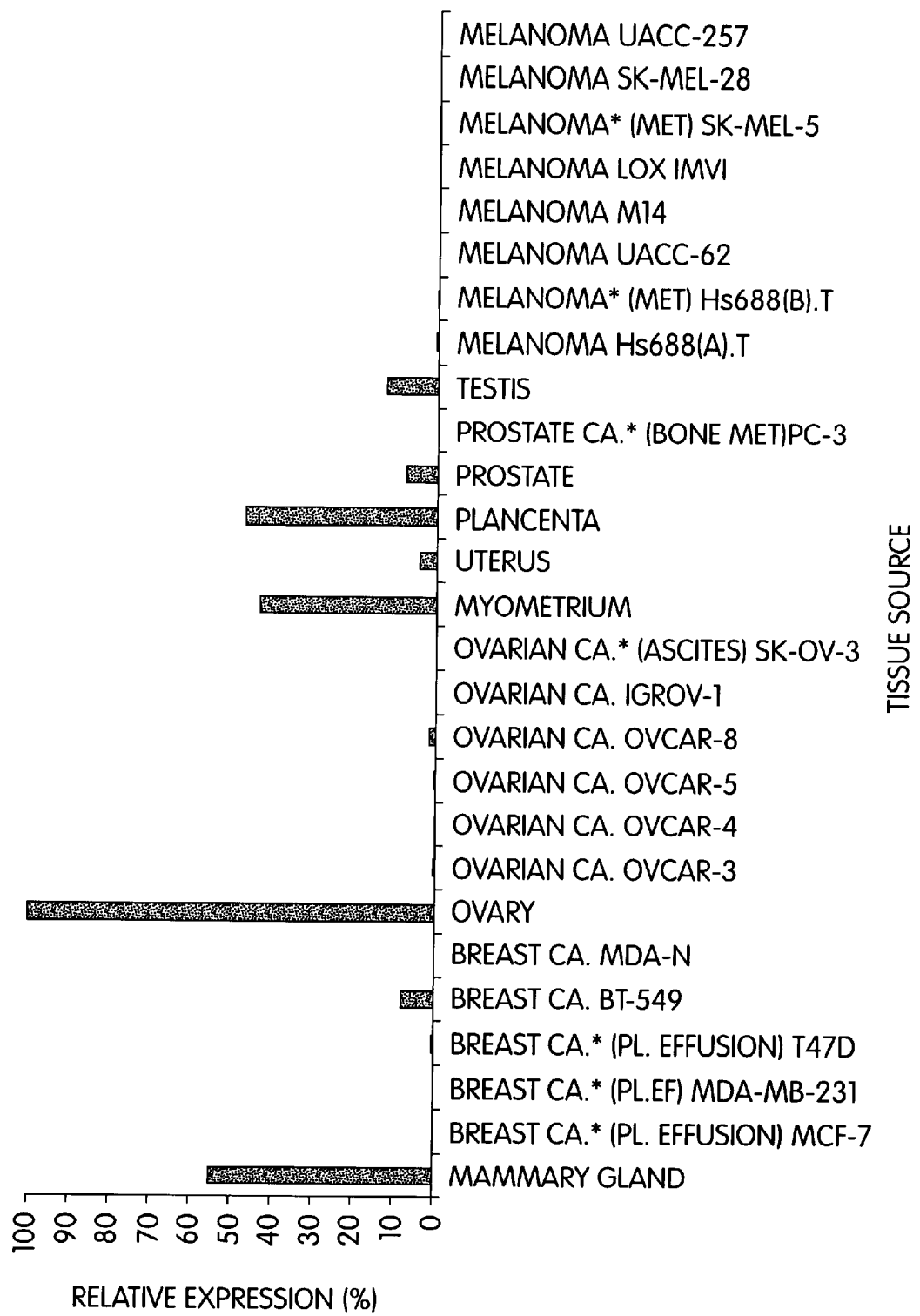

The results for probe set Ag86 are presented in FIGS. 6A–C. Highest expression was found in the normal tissues fetal kidney, ovary, mammary gland, placenta and myometrium, with moderate levels of expression in other normal tissues. Use of probe set AG86b detected high expression levels in the same tissues as well as adipose, and moderate levels in other normal tissues (FIGS. 7A–C).

For cloneAL035460A, the following primers and probes, which detect positions 588–663 in the clone, were used:

Ag 2(F): 5'-GTGCTGCTGCTCTACAATAACCA-3' (SEQ ID NO:25)

Ag 2(R): 5'-GTTTCTGCAGCTGGGCCAT-3' (SEQ ID NO:26)

Ag 2(P):-FAM-5'-TGGACCGGTGCGCCTTCGAT-3'-TAMRA (SEQ ID NO:27)

The results are shown in FIGS. 7A–7C. High expression of cloneAL035460A was found in most normal brain tissues tested. In addition, low levels of expression are found in many other normal tissues and certain cancer tissues.

EXAMPLE 5

Suppression of Tumor Growth by AL035460

Breast and ovarian tumor cell lines are transfected with the AL035460A gene under the control of an inducible promoter. Cell lines that may be used include breast carcinoma (pleural effusion) MCF-7, breast carcinoma (pleural effusion) MDA-MB-23 1, breast carcinoma (pleural effusion) T47D, breast carcinoma BT-549, breast carcinoma MDA-N, ovarian carcinoma OVCAR-3, ovarian carcinoma OVCAR-4, ovarian carcinoma OVCAR-5, ovarian carcinoma OVCAR-8, ovarian carcinoma IGROV-1, and ovarian carcinoma (ascites) SK-OV-3; these cell lines show reduced expression of AL035460A. Stable transfectants are to be generated using methods based, for example, on incorporating the AL035460A gene into a mammalian expression vector such as pCDM8 (Seed (1987) *Nature* 329:840) or pMT2PC (Kaufman et al. (1987) *EMBO J* 6: 187–195). An inducible promoter may be chosen from among those reviewed in Saez E, et al. (Inducible gene expression in mammalian cells and transgenic mice. Curr Opin Biotechnol 1997 October;8(5):608–16). For other suitable expression systems for eukaryotic cells are described, e.g., in Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989. Stable genetic transformation of mammalian cells is also described by Sawada M, and Kamataki T. (Genetically engineered cells stably expressing cytochrome P450 and their application to mutagen assays. Mutat Res. 1998 August;411 (1):19–43) and DeCruz E E, et al. (The basis for somatic gene therapy of cancer. J Exp Ther Oncol. 1996 March; 1(2):73–83). Transfection may be effected, for example, by liposome-mediated transfection (Schenborn E T, and Oler J. Methods Mol Biol. 2000;130:155–64), DEAE-dextran transfection (Schenborn E T, and Goiffon V. Methods Mol Biol. 2000;130:147–53) or calcium phosphate transfection (Schenborn E T, and Goiffon V. (Methods Mol Biol. 2000;130:135–45).

After transfecting the cells, the effect of the AL035460A gene product on cell growth is be assessed following induction. Both in vitro and in vivo growth is to be monitored and compared to growth of tumor cells transfected with empty vector. It is expected that the transfected tumor cells will exhibit a decrease in growth rate both in vitro and in vivo following expression of AL035460A.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polypeptide consisting of the amino acid sequence of SEQ ID NO:2, or a mature form thereof.

2. An isolated polypeptide comprising the amino acid sequence of SEQ ID NO:2, or a mature form thereof, wherein said polypeptide has carboxypeptidase activity.

* * * * *